(12) United States Patent
Guan et al.

(10) Patent No.: US 10,045,986 B2
(45) Date of Patent: Aug. 14, 2018

(54) METHOD, DEVICE, AND SYSTEM FOR RADIO RESOURCE MANAGEMENT MEASUREMENT

(71) Applicant: Huawei Technologies Co., Ltd., Shenzhen (CN)

(72) Inventors: Lei Guan, Beijing (CN); Lixia Xue, Beijing (CN); David Jean-Marie Mazzarese, Beijing (CN)

(73) Assignee: Huawei Technologies Co., Ltd., Shenzhen (CN)

( * ) Notice: Subject to any disclaimer, the term of this patent is extended or adjusted under 35 U.S.C. 154(b) by 80 days.

(21) Appl. No.: 15/140,299

(22) Filed: Apr. 27, 2016

(65) Prior Publication Data
US 2016/0242083 A1 Aug. 18, 2016

Related U.S. Application Data

(63) Continuation of application No. PCT/CN2014/071572, filed on Jan. 27, 2014.

(30) Foreign Application Priority Data

Oct. 28, 2013 (WO) ............... PCT/CN2013/086089
Nov. 21, 2013 (WO) ............... PCT/CN2013/087638

(51) Int. Cl.
*H04W 4/00* (2018.01)
*A61K 31/506* (2006.01)
(Continued)

(52) U.S. Cl.
CPC ........ *A61K 31/506* (2013.01); *A61K 31/4166* (2013.01); *A61K 31/4439* (2013.01);
(Continued)

(58) Field of Classification Search
CPC .. H04W 36/0072; H04W 24/08; H04W 36/04
(Continued)

(56) References Cited

U.S. PATENT DOCUMENTS

2010/0309797 A1 12/2010 Lindoff et al.
2011/0310753 A1* 12/2011 Chou ............... H04W 48/16
370/252

(Continued)

FOREIGN PATENT DOCUMENTS

CN 101932073 A 12/2010
CN 102461023 A 5/2012
(Continued)

OTHER PUBLICATIONS

"Discussion on discovery and measurement of turned-off small cells," 3GPP TSG RAN WG1 Meeting #74 bis, R1-134257, pp. 1-5, Guangzhou, China, $3^{rd}$ Generation Partnership Project, Valbonne, France (Oct. 7-11, 2013).
(Continued)

*Primary Examiner* — Chi H Pham
*Assistant Examiner* — Alexander O Boakye
(74) *Attorney, Agent, or Firm* — Leydig, Voit & Mayer, Ltd.

(57) ABSTRACT

Embodiments provide a method for radio resource management measurement. The method includes: determining, by a UE according to a detected first reference signal, a first resource on which the detected first reference signal is located; determining, by the UE, a reference signal received power RSRP of a target cell according to a received power of the detected first reference signal carried on the first resource; determining, by the UE, a second resource; determining, by the UE, a received signal strength indicator RSSI of the target cell according to a total received power on the second resource; and determining, by the UE, reference
(Continued)

signal received quality RSRQ or a signal to interference plus noise ratio SINR of the target cell or both according to the RSRP and RSSI. The method is applied to radio resource management measurement.

18 Claims, 11 Drawing Sheets

(51) Int. Cl.

| | | |
|---|---|---|
| *C07D 239/22* | (2006.01) | |
| *C07D 401/04* | (2006.01) | |
| *C07D 403/04* | (2006.01) | |
| *C07D 233/72* | (2006.01) | |
| *A61K 31/4166* | (2006.01) | |
| *A61K 31/4439* | (2006.01) | |
| *C07D 239/47* | (2006.01) | |
| *C07D 233/76* | (2006.01) | |
| *C07D 213/643* | (2006.01) | |

(52) U.S. Cl.
CPC ......... *C07D 233/72* (2013.01); *C07D 233/76* (2013.01); *C07D 239/22* (2013.01); *C07D 239/47* (2013.01); *C07D 401/04* (2013.01); *C07D 403/04* (2013.01); *C07D 213/643* (2013.01)

(58) Field of Classification Search
USPC ....................................................... 370/332
See application file for complete search history.

(56) References Cited

U.S. PATENT DOCUMENTS

| | | |
|---|---|---|
| 2012/0147772 A1 | 6/2012 | Kazmi et al. |
| 2013/0301456 A1 | 11/2013 | Siomina et al. |
| 2014/0241198 A1 | 8/2014 | Sun et al. |
| 2014/0362793 A1 | 12/2014 | Chai et al. |
| 2015/0029885 A1 | 1/2015 | Seo et al. |

FOREIGN PATENT DOCUMENTS

| | | |
|---|---|---|
| CN | 102624494 A | 8/2012 |
| CN | 102948087 A | 2/2013 |
| CN | 103107873 A | 5/2013 |
| CN | 103220066 A | 7/2013 |
| CN | 103262460 A | 8/2013 |
| WO | WO 2012115366 A1 | 8/2012 |
| WO | WO 2013133605 A1 | 9/2013 |

OTHER PUBLICATIONS

"RSSI measurements for small cell on/off Operation," 3GPP TSG RAN WG1 Meeting #77, RI-141936, pp. 1-4, Seoul, Korea, $3^{rd}$ Generation Partnership Project, Valbonne, France (May 19-23, 2014).

"3rd Generation Partnership Project; Technical Specification Group Radio Access Network; Evolved Universal Terrestrial Radio Access (E-UTRA); Physical channels and modulation (Release 11)," 3GPP TS 36.211, V11.4.0, pp. 1-120, $3^{rd}$ Generation Partnership Project, Valbonne, France (Sep. 2013).

"3rd Generation Partnership Project; Technical Specification Group Radio Access Network; Evolved Universal Terrestrial Radio Access (E-UTRA); Physical layer procedures (Release 11)," 3GPP TS 36.213, V11.4.0, pp. 1-182, $3^{rd}$ Generation Partnership Project, Valbonne, France (Sep. 2013).

"3rd Generation Partnership Project; Technical Specification Group Radio Access Network; Evolved Universal Terrestrial Radio Access (E-UTRA); Physical layer; Measurements (Release 11)," 3GPP TS 36.214, V11.1.0, pp. 1-14, $3^{rd}$ Generation Partnership Project, Valbonne, France (Dec. 2012).

"3rd Generation Partnership Project; Technical Specification Group Radio Access Network; Evolved Universal Terrestrial Radio Access (E-UTRA) and Evolved Universal Terrestrial Radio Access Network (E-UTRAN); Overall description; Stage 2 (Release 11)," 3GPP TS 36.300, V11.7.0, pp. 1-209, $3^{rd}$ Generation Partnership Project, Valbonne, France (Sep. 2013).

"3rd Generation Partnership Project; Technical Specification Group Radio Access Network; Evolved Universal Terrestrial Radio Access (E-UTRA); Radio Resource Control (RRC); Protocol specification (Release 11)," 3GPP TS 36.331, V11.5.0, pp. 1-347, $3^{rd}$ Generation Partnership Project, Valbonne, France (Sep. 2013).

* cited by examiner

METHOD, DEVICE, AND SYSTEM FOR RADIO RESOURCE MANAGEMENT MEASUREMENT

CROSS-REFERENCE TO RELATED APPLICATIONS

This application is a continuation of International Patent Application No. PCT/CN2014/071572, filed on Jan. 27, 2014, which claims priority to International Patent Application No. PCT/CN2013/086089, filed on Oct. 28, 2013, and International Patent Application No. PCT/CN2013/087638, filed on Nov. 21, 2013, all of which are incorporated herein by reference in their entireties.

TECHNICAL FIELD

The present disclosure relates to the field of communications, and in particular, to a method, a device, and a system for radio resource management measurement.

BACKGROUND

An LTE (Long Term Evolution) system is based on the OFDM (orthogonal frequency division multiplexing) technology, and the OFDM technology is used to divide time-frequency resources into OFDM symbols in the time domain and OFDM subcarriers in the frequency domain. To maintain service transmission in the LTE system, a UE needs to perform synchronization, channel state measurement, and RRM (radio resource management) measurement according to a reference signal transmitted by a base station. Specifically, the RRM measurement includes measurement of an RSRP (reference signal received power), RSRQ (reference signal received quality), and RSSI (received signal strength indicator). The RSRP represents an average received power of CRSs that are transmitted by a target measured cell and carried on CRS (cell-specific reference signal) resource elements of the target measured cell; the RSSI represents an average received power of all signals in OFDM symbols in which the CRSs of the target measured cell are located; and the RSRQ is obtained according to a ratio of the RSRP to the RSSI. In addition, the conventional LTE system has a relatively high requirement on power efficiency of a base station, and in future network topology evolution, an operator will deploy a large number of heterogeneous networks. For this reason, a current mainstream heterogeneous network includes a macro base station and a large number of small cells within a range of the macro base station.

In the heterogeneous network that is densely populated with small cells, there is no UE to be served within a range of many small cells, due to high density of network devices. In addition, when all the small cells are in an enabled state, even if no service is transmitted, each small cell still transmits reference information at short intervals, for example, a PSS (primary synchronization signal), an SSS (secondary synchronization signal), a CRS (cell-specific reference signal), and an RCRS (reduced cell-specific reference signal), where a transmission interval of the PSS/SSS/RCRS is 5 subframes, and a transmission interval of the CRS is 1 subframe. The reference information causes strong inter-cell interference. A potential solution is to disable the small cells in which no UE is served, so that these small cells do not transmit the reference information at short intervals, thereby achieving an effect of saving power and reducing inter-cell interference.

However, it is found that disabling or enabling the foregoing small cells causes an interference environment between neighboring cells in an area to change or vary quickly. This increases difficulty in RRM measurement, and imposes a higher requirement on RRM measurement, and the UE is unable to efficiently perform a cell selection, reselection, or handover for a local cell and a neighboring cell.

SUMMARY

Embodiments of the present disclosure provide a method, a device, and a system for radio resource management measurement, which are capable of improving efficiency and accuracy of radio resource management measurement.

To achieve the foregoing objectives, the embodiments of the present disclosure use the following technical solutions:

According to a first aspect, a user equipment is provided and includes:

a determining unit, configured to detect a first reference signal, and determine, according to the detected first reference signal, a first resource on which the detected first reference signal is located;

a first power determining unit, configured for the UE to determine a reference signal received power RSRP of a target cell according to a received power of the detected first reference signal carried on the first resource;

the determining unit, further configured to determine a second resource, where the second resource and the first resource occupy different times, and the second resource is used to carry second reference information when the target cell or a neighboring cell of the target cell are in an active state, or the second resource is used to carry second reference information when the target cell or a neighboring cell of the target cell or both are in a dormant state and used to carry the second reference information when the target cell changes from the dormant state to the active state;

a second power determining unit, configured to determine a received signal strength indicator RSSI of the target cell according to a total received power on the second resource, where the first resource and the second resource are at different times; and a third power determining unit, configured to determine reference signal received quality RSRQ or a signal to interference plus noise ratio SINR of the target cell according to the RSRP and RSSI.

According to the first aspect, in a first possible implementation, the determining unit is further configured to determine, according to the detected first reference signal, the target cell corresponding to the detected first reference signal.

According to the first aspect, in a second possible implementation manner, the determining unit is further configured to detect a third reference signal, and determine, according to the detected third reference signal, a target cell corresponding to the detected third reference signal.

According to the first possible implementation, in a third possible implementation, the UE further includes:

an information acquiring unit, configured to acquire configuration information of the first reference signal, where the configuration information includes a candidate sequence of the first reference signal or a candidate time-frequency resource of the first reference signal or both;

the determining unit is specifically configured to: detect the first reference signal according to the configuration information of the first reference signal; and determine, according to the configuration information of the first reference signal, the first resource on which the first reference signal is located.

According to the first aspect or any one of the first to third possible implementations thereof, in a fourth possible implementation, the second resource and the first resource are at different times.

According to the first aspect or any one of the first to third possible implementations thereof, in a fifth possible implementation, the number of time units included in the second resource is greater than the number of time units included in the first resource, and the time units included in the second resource are inclusive of the time units included in the first resource, where each of the time units includes any one of an OFDM symbol, a timeslot, a subframe, and a subframe set.

According to the first aspect or any one of the first to fifth possible implementations thereof, in a sixth possible implementation, the determining unit is specifically configured to determine the second resource according to the first resource and a resource offset, where the resource offset includes a time-domain offset or a frequency offset or both, and the resource offset is pre-configured or is notified by the base station.

According to the fourth possible implementation, in a seventh possible implementation, that the first resource and the second resource are at different times specifically includes the following: the first resource and the second resource belong to different orthogonal frequency division multiplexing OFDM symbols or different timeslots or different subframes or different subframe sets.

According to the first aspect or any one of the first to seventh possible implementations thereof, in an eighth possible implementation, the third power determining unit is specifically configured to: if a transmit power of the target cell on the second resource is not 0, determine the RSRQ of the target cell according to the RSRP and RSSI; and/or if a transmit power of the target cell on the second resource is 0, determine the SINR of the target cell according to the RSRP and RSSI.

According to the first aspect or any one of the first to eighth possible implementations thereof, in a ninth possible implementation, the first reference signal includes a discovery reference signal DRS; and the second reference information includes at least one of a CSI-RS, a CRS, an RCRS, a PSS, an SSS, a PRS, and a broadcast channel.

According to the first aspect or any one of the first to ninth possible implementations thereof, in a tenth possible implementation, where the UE further includes:

an information reporting unit is configured to report the RSRQ to the base station, so that the base station determines, according to the RSRQ reported by the UE, whether to switch the target cell from the dormant state to the active state, and/or determines, according to the RSRQ reported by the UE, whether to configure the target cell for the UE.

According to the first aspect or any one of the first to ninth possible implementations thereof, in an eleventh possible implementation, an information reporting unit is configured to report the SINR to the base station, so that the base station determines, according to the SINR reported by the UE, whether to switch the target cell from the dormant state to the active state, and/or determines, according to the SINR reported by the UE, whether to configure the target cell for the UE.

According to the first aspect or any one of the first to ninth possible implementations thereof, in a twelfth possible implementation, an information reporting unit is configured to report the RSRQ and SINR to the base station, so that the base station determines, according to the RSRQ and SINR reported by the UE, whether to switch the target cell from the dormant state to the active state, and/or determines, according to the RSRQ and SINR reported by the UE, whether to configure the target cell for the UE.

According to a second aspect, a method for radio resource management measurement is provided and includes:

detecting, by a user equipment UE, a first reference signal, and determining, according to the detected first reference signal, a first resource on which the detected first reference signal is located;

determining, by the UE, a reference signal received power RSRP of a target cell according to a received power of the detected first reference signal carried on the first resource;

determining, by the UE, a second resource, where the second resource and the first resource occupy different times, and the second resource is used to carry second reference information when the target cell or a neighboring cell of the target cell or both are in an active state, or the second resource is used to not carry the second reference information when the target cell or a neighboring cell of the target cell or both are in a dormant state and used to carry the second reference information when the target cell changes from the dormant state to the active state;

determining, by the UE, a received signal strength indicator RSSI of the target cell according to a total received power on the second resource, where the first resource and the second resource are at different times; and determining, by the UE, reference signal received quality RSRQ or a signal to interference plus noise ratio SINR of the target cell or both according to the RSRP and RSSI.

According to the second aspect, in a first possible implementation, the method further includes:

determining, by the UE according to the detected first reference signal, the target cell corresponding to the detected first reference signal.

According to the second aspect, in a second possible implementation, the method further includes:

detecting, by the UE, a third reference signal, and determining, according to the detected third reference signal, a target cell corresponding to the detected third reference signal.

According to the first possible implementation, in a third possible implementation, acquiring, by the UE, configuration information of the first reference signal, where the configuration information includes a candidate sequence of the first reference signal or a candidate time-frequency resource of the first reference signal or both; and the detecting, by a user equipment UE, a first reference signal, and determining, according to the detected first reference signal, a first resource on which the detected first reference signal is located, includes:

detecting, by the UE, the first reference signal according to the configuration information of the first reference signal; and determining, by the UE according to the configuration information of the detected first reference signal, the first resource on which the detected first reference signal is located.

According to the second aspect or any one of the first to third possible implementations thereof, in a fourth possible implementation, the second resource and the first resource are at different times.

According to the second aspect or any one of the first to third possible implementations thereof, in a fifth possible implementation, the number of time units included in the second resource is greater than the number of time units included in the first resource, and the time units included in the second resource are inclusive of the time units included in the first resource, where each of the time units is any one of an OFDM symbol, a timeslot, a subframe, and a subframe set.

According to the second aspect or any one of the first to fifth possible implementations thereof, in a sixth possible implementation, the determining, by the UE, a second resource, includes:

determining, by the UE, the second resource according to the first resource and a resource offset, where the resource offset includes a time-domain offset or a frequency offset or both, and the resource offset is pre-configured or is notified by the base station.

According to the fourth possible implementation, in a seventh possible implementation, that the first resource and the second resource are at different times specifically includes the following: the first resource and the second resource belong to different orthogonal frequency division multiplexing OFDM symbols or different timeslots or different subframes or different subframe sets.

According to the second aspect or any one of the first to seventh possible implementations thereof, in an eighth possible implementation, the determining, by the UE, reference signal received quality RSRQ or a signal to interference plus noise ratio SINR of the target cell or both according to the RSRP and RSSI, includes:

if a transmit power of the target cell on the second resource is not 0, determining, by the UE, the RSRQ of the target cell according to the RSRP and RSSI; and/or if a transmit power of the target cell on the second resource is 0, determining, by the UE, the SINR of the target cell according to the RSRP and RSSI.

According to the second aspect or any one of the first to eighth possible implementations thereof, in a ninth possible implementation, the first reference signal includes a discovery reference signal DRS; and the second reference information includes at least one of a CSI-RS, a CRS, an RCRS, a PSS, an SSS, a PRS, and a broadcast channel.

According to the second aspect or any one of the first to ninth possible implementations thereof, in a tenth possible implementation, after the determining, by the UE, reference signal received quality RSRQ or a signal to interference plus noise ratio SINR of the target cell or both according to the RSRP and RSSI, the method further includes:

reporting, by the UE, the RSRQ to the base station, so that the base station determines, according to the RSRQ reported by the UE, whether to switch the target cell from the dormant state to the active state, and/or determines, according to the RSRQ reported by the UE, whether to configure the target cell for the UE.

According to the second aspect or any one of the first to ninth possible implementations thereof, in an eleventh possible implementation, after the determining, by the UE, reference signal received quality RSRQ or a signal to interference plus noise ratio SINR of the target cell or both according to the RSRP and RSSI, the method further includes:

reporting, by the UE, the SINR to the base station, so that the base station determines, according to the SINR reported by the UE, whether to switch the target cell from the dormant state to the active state, and/or determines, according to the SINR reported by the UE, whether to configure the target cell for the UE.

According to the second aspect or any one of the first to ninth possible implementations thereof, in a twelfth possible implementation, after the determining, by the UE, reference signal received quality RSRQ or a signal to interference plus noise ratio SINR of the target cell or both according to the RSRP and RSSI, the method further includes:

reporting, by the UE, the RSRQ and SINR to the base station, so that the base station determines, according to the RSRQ and SINR reported by the UE, whether to switch the target cell from the dormant state to the active state, and/or determines, according to the RSRQ and SINR reported by the UE, whether to configure the target cell for the UE.

In the method, equipment, and system for radio resource management measurement according to the embodiments of the present disclosure, reference signal received quality RSRQ or a signal to interference plus noise ratio SINR of a target cell or both are determined according to a reference signal received power RSRP of the target cell, which is determined by a received power of a first reference signal carried on a first resource, and a received signal strength indicator RSSI of the target cell, which is determined by a total received power on a second resource. In comparison with the prior art in which the RSRQ or SINR of a target cell is measured only according to a CRS and an interference environment between neighboring cells in an area is caused to change or vary quickly, the method for radio resource management measurement according to the present disclosure achieves higher efficiency and higher accuracy.

BRIEF DESCRIPTION OF DRAWINGS

To describe the technical solutions in the embodiments of the present disclosure more clearly, the following briefly introduces the accompanying drawings required for describing the embodiments. Apparently, the accompanying drawings in the following description show merely some embodiments of the present disclosure, and persons of ordinary skill in the art may still derive other drawings from these accompanying drawings without creative efforts.

DESCRIPTION OF EMBODIMENTS

Figure 1:
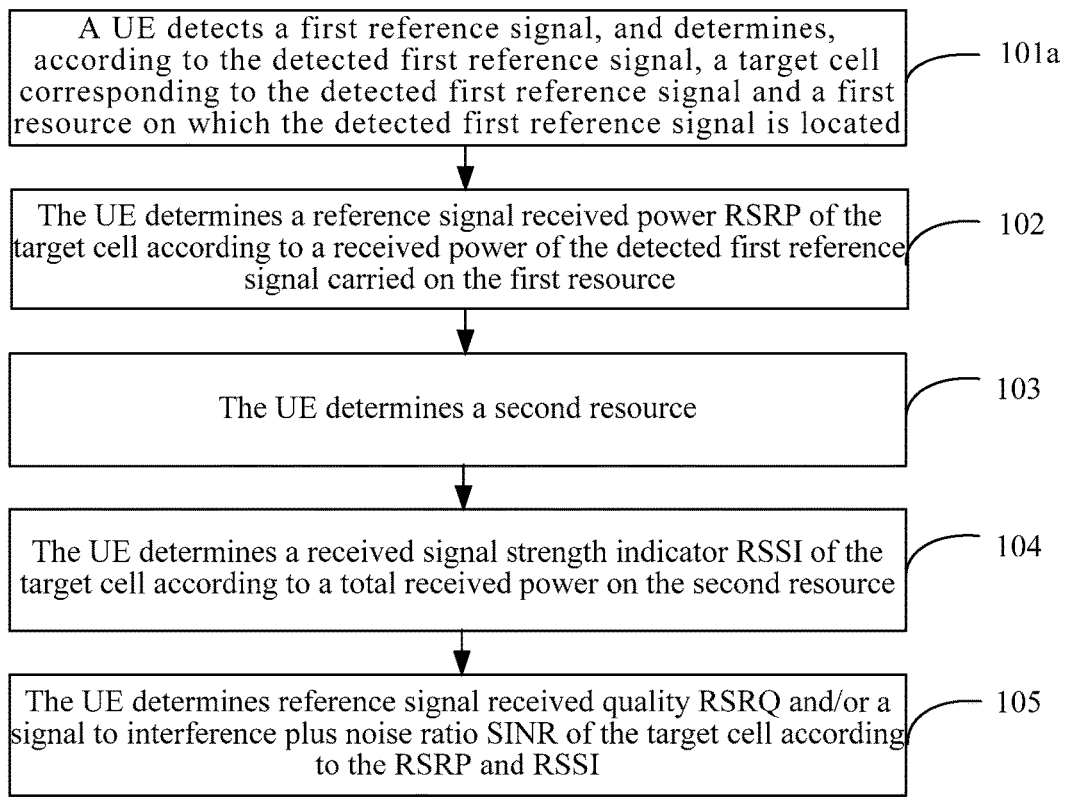
FIG. 1 is a schematic flowchart of a method for radio resource management measurement according to an embodiment of the present disclosure.

The following clearly describes the technical solutions in the embodiments of the present disclosure with reference to the accompanying drawings in the embodiments of the present disclosure. Apparently, the described embodiments are merely a part rather than all of the embodiments of the present disclosure. All other embodiments obtained by persons of ordinary skill in the art based on the embodiments of the present disclosure without creative efforts shall fall within the protection scope of the present disclosure.

The embodiments provided by the present disclosure are applied to an LTE system. The LTE system is based on the OFDM technology, and the OFDM technology is used to divide time-frequency resources into OFDM symbols in the time domain and OFDM subcarriers in the frequency domain. A smallest resource granularity formed thereby is referred to as an RE (resource element), where the resource element represents a time-frequency grid point formed by an OFDM symbol in the time domain and an OFDM subcarrier in the frequency domain. Meanwhile, service transmission in the LTE system is based on scheduling by a base station. Generally, the base station transmits a control channel, where the control channel may carry scheduling information of an uplink or downlink data channel, and the scheduling information includes control information such as resource allocation information or a modulation and coding scheme. After receiving the scheduling information carried by the control channel, a UE (user equipment) performs reception of the downlink data channel or transmission of the uplink data channel according to the scheduling information. The UE scheduling by the base stations on a basis of resource block (RB). A resource block occupies a length of a subframe in the time domain, and occupies a width of 12 OFDM subcarriers in the frequency domain. A subframe generally includes 14 OFDM symbols.

Further, to maintain service transmission in the LTE system, the UE needs to perform synchronization, channel state measurement, and RRM (radio resource management) measurement according to a reference signal transmitted by the base station. The synchronization is classified into initial coarse synchronization and precise synchronization by time-frequency tracking. The initial coarse synchronization is performed according to a PSS and an SSS transmitted by the base station, while the precise synchronization by time-frequency tracking is performed according to a CRS (cell-specific reference signal) transmitted by the base station. The channel state measurement includes channel measurement and interference measurement. Generally, the measurement is performed according to a CRS or an RCRS. The RCRS is a CRS of N ms, which is obtained by modifying an interval of a CRS from every subframe to every N ms, where N may be 5 or any other integer. This means that in the LTE system, a CRS may not be transmitted in every subframe, but is transmitted at an interval of N ms (N>1). At this time, the CRS is referred to as an RCRS. The RRM measurement includes measurement of an RSRP (reference signal received power), RSRQ (reference signal received quality), and RSSI (received signal strength indicator). The RSRP represents an average received power of CRSs that are carried on CRS (cell-specific reference signal) resource elements of a target measured cell and transmitted by the target measured cell; the RSSI represents an average received power of all signals in OFDM symbols in which the CRSs of the target measured cell are located, including an average power of all signals such as a signal of a local cell, a signal of an intra-frequency neighboring cell, a signal spilled over from another frequency band to a local frequency band, and thermal noise; and the RSRQ is obtained according to a ratio of the RSRP to the RSSI.

In addition, the conventional LTE system has a relatively high requirement on power efficiency of the base station, and in future network topology evolution, an operator will deploy a large number of heterogeneous networks. For this reason, a current mainstream heterogeneous network includes a macro base station and a large number of small cells within a range of the macro base station. The macro base station mainly provides coverage and real-time data services. The small cells mainly provide high-speed data services. Furthermore, the macro base station and the small cells may be deployed to use a same frequency or different frequencies, but in most scenarios, they are deployed to use different frequencies. Moreover, in the heterogeneous network that is densely populated with small cells, there is no UE to be served within a range of a large number of small cells, due to high density of network devices. When all the small cells are in an enabled state, even if no service is transmitted, each small cell still transmits reference information at short intervals (for example, a PSS, an SSS, a CRS, and an RCRS, where a transmission period of the PSS/SSS/RCRS is 5 subframes, and a transmission interval of the CRS is 1 subframe). The reference information causes strong inter-cell interference. A potential solution is to disable the small cells in which no UE is served, so that these small cells do not transmit the reference information at short intervals, thereby achieving an effect of saving power and reducing inter-cell interference. However, the inventor finds that disabling or enabling the foregoing small cells causes an interference environment between neighboring cells in an area to change or vary quickly. This increases difficulty in RRM measurement, and imposes a higher requirement on RRM measurement, and the UE is unable to efficiently perform a cell selection, reselection, or handover for a local cell and a neighboring cell. Therefore, how to perform RRM measurement more efficiently is a primary problem to be solved so far.

In the foregoing technical solution, if these small cells in which no UE is served are all disabled, a UE is unable to quickly discover these disabled small cells, and unable to perform RRM measurement for these disabled small cells, either. Consequently, these small cells are unable to determine when they will be enabled again. Therefore, based on the foregoing solution, a preferable solution is to allow these small cells in which no UE is served to transmit a DRS (discovery reference signal) at a relatively long interval, so that UEs around these disabled small cells may quickly discover these disabled small cells according to the DRS, and perform RRM measurement. Furthermore, to reduce power consumption when a UE uses a DRS to perform RRM measurement, multiple small cells are generally allowed to synchronously transmit a DRS, so that the UE only needs to use the DRS in this time window to perform RRM measurement to acquire RRM measurement results of the multiple small cells simultaneously. For ease of understanding, in the following description in this specification, the foregoing state in which a cell is disabled but transmits a DRS is referred to as a dormant state, and at this time, short-interval reference signals, including at least one of a PSS, an SSS, a CRS/RCRS, and a CSI-RS which is used for CSI measurement, are not transmitted, or other signals except the DRS are not transmitted; and the state in which a cell normally serves a UE after being enabled is referred to as an active state, and at this time, it is necessary to transmit at least one of a PSS, an SSS, a CRS/RCRS, and a CSI-RS which is used for CSI measurement.

In addition, based on the foregoing description, when neighboring small cells of the target measured cell include a lot of small cells in the dormant state, transmit powers of these small cells in the dormant state are not 0 when they synchronously transmit a DRS at a relatively long interval, but their transmit powers are 0 in other periods. Due to the synchronous DRS transmission mechanism, the transmit powers of these small cells at the time of transmitting a DRS are counted into an RSSI, and therefore an RSSI value is overestimated, and further, an RSRQ or SINR value obtained by using the RSSI is underestimated. Therefore, the inventor finds that, regardless of whether the target measured cell is in the active state or dormant state when RRM measurement is performed according to a DRS, the RSRQ or SINR of the target measured cell, which is measured according to the DRS, is underestimated, and consequently, a small cell is unable to serve the UE as expected although it is in good condition.

Figure 2:
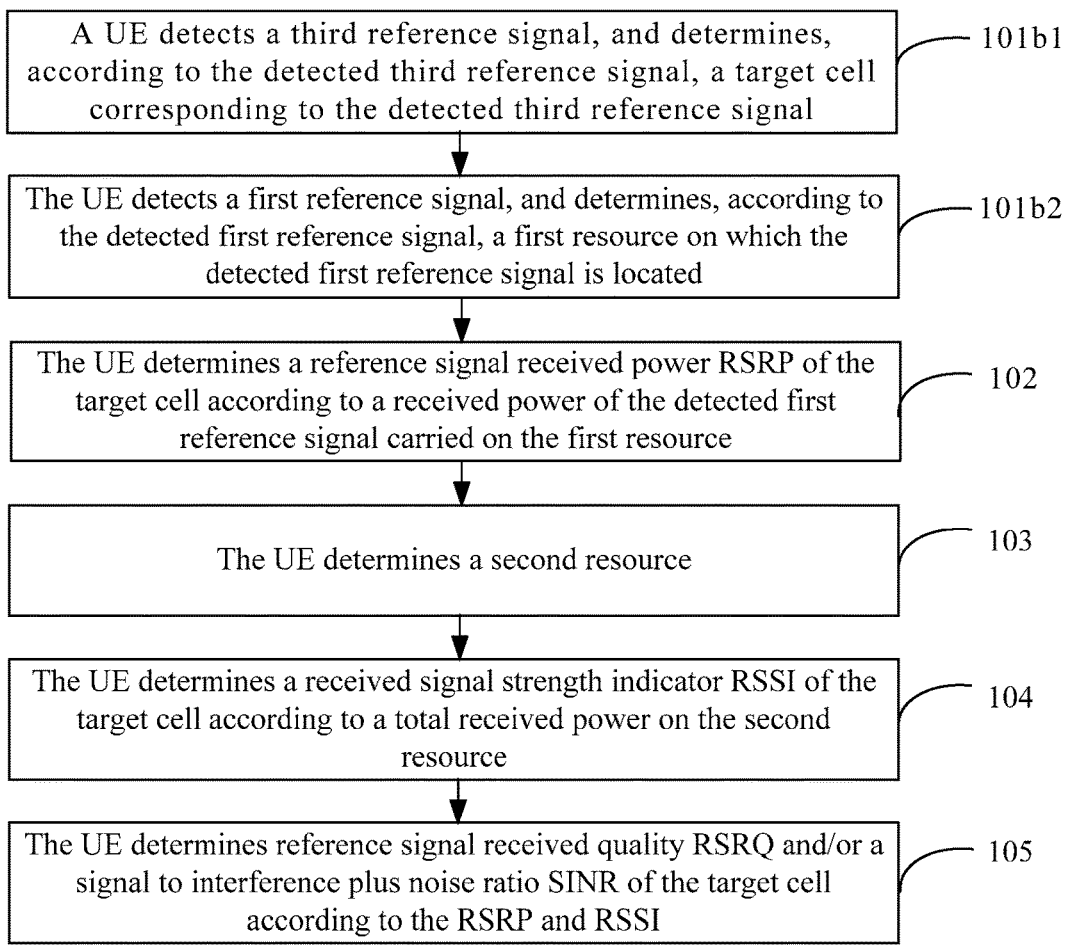
FIG. 2 is a schematic flowchart of another method for radio resource management measurement according to an embodiment of the present disclosure.

Therefore, in view of the application scenario in which the RSRQ or SINR value is underestimated, an embodiment of the present invention provides a method for radio resource management measurement. The method is applied to a user equipment side. As shown in FIG. 1 and FIG. 2, the method for radio resource management measurement specifically includes the following steps:

101a. A UE detects a first reference signal, and determines, according to the detected first reference signal, a target cell corresponding to the detected first reference signal and a first resource on which the detected first reference signal is located.

The first reference signal is a DRS, and generally its transmission interval is relatively long, for example, longer than 5 ms or 10 ms, dozens or hundreds of ms or even thousands of ms. The DRS is used to measure an RSRP, and is located on the first resource. The DRS may be specifically designed based on a conventional reference signal, for example, based on at least one of a PRS, a CSI-RS, a CRS, an RCRS, a PSS, and an SSS. Alternatively, some optimization may be performed based on the foregoing conventional reference signal, for example, a sequence of the conventional reference signal remains unchanged, but a time-frequency resource of the conventional reference signal is configured flexibly before the conventional reference signal is used as the DRS. In addition, the first resource on which the detected first reference signal is located may be a resource element that carries the detected first reference signal. Therefore, after detecting the first reference signal, the UE may determine the resource element of the detected first reference signal as the first resource.

It should be noted that, when the UE determines a cell identifier of the target cell and the first resource, the determining may be performed according to a same reference signal (that is, the first reference signal) as shown in step 101a, and may also be performed by using respective different reference signals as shown in the following steps 101b1 and 101b2. That is, steps 101b1 and 101b2 may replace step 101a.

As shown in FIG. 2, a specific implementation manner of steps 101b1 and 101b2 is as follows:

101b1. The UE detects a third reference signal, and determines, according to the detected third reference signal, a target cell corresponding to the detected third reference signal.

101b2. The UE detects a first reference signal, and determines, according to the detected first reference signal, a first resource on which the detected first reference signal is located.

The third reference signal in steps 101b1 and 101b2 may be a synchronization signal, that is, a PSS or an SSS or a combination thereof. The synchronization signal may also be regarded as a DRS or a part of a DRS. At this time, the UE may determine the cell identifier of the target cell according to the detected PSS or SSS or both. Correspondingly, the first reference signal used for the UE to determine the first resource in step 101b2 may be at least one of a PRS, a CSI-RS, a CRS, and an RCRS. The first reference signal may be regarded as a DRS or another part of a DRS, and the first reference signal is used for RRM measurement of the target cell. For details, reference may be made to the following steps:

102. The UE determines a reference signal received power RSRP of the target cell according to a received power of the detected first reference signal carried on the first resource.

103. The UE determines a second resource.

When the target cell is in an active state, the target cell transmits at least second reference information on the second resource; and/or, when the target cell is in a dormant state, the target cell transmits the detected first reference signal on the first resource, and transmits no second reference information on the second resource, but when the target cell changes from the dormant state to the active state, the target cell transmits the second reference information on the second resource. The foregoing feature of the second resource regarding whether or not to carry the second reference information is also applicable to a neighboring cell of the target cell.

Optionally, the second resource is only required to not carry the first reference signal, that is, the second resource is any resource that does not carry the first reference signal, and may or may not carry the second reference information. If the second reference information is not carried, the power on the second resource is determined according to a dynamically scheduled data channel, that is, if data is scheduled, there is a power, or otherwise, there may be no power. In this way, an impact of interference caused by a data channel may be reflected more accurately. Apparently, if the second resource carries the second reference information, the second reference information does not depend on dynamic data scheduling, and the second reference information may be transmitted providing that the target cell is in the active state. In this case, the measured interference may not accurately reflect the interference caused by a data channel, but the measured interference is stable and does not vary greatly, so that a network side can make use of the measurement result from the UE, for example, add or remove a cell or perform a handover for the UE.

The second resource refers to all or a part of resource elements in an entire OFDM symbol in which the second reference information of the target cell is located, and may also be a timeslot or a subframe in which the second reference information is located, or multiple OFDM symbols in a subframe set in which the second reference information is located. The second reference information includes at least one of a CSI-RS, a CRS, an RCRS, a PSS, an SSS, a PRS, and a broadcast channel. Specifically, when the target cell is in the active state, the target cell transmits at least the second reference information on the second resource; and when the target cell is in the dormant state, because the target cell does not transmit the second reference information, that is, only the first reference signal exists in a transmission frame of the target cell, the target cell transmits the first reference signal on the first resource, and does not transmit the second reference information on the second resource, or the second resource is a resource on which the second reference information is transmitted when the target cell is in the active state. In addition, the second reference information may also be downlink data. Because the downlink data is dynamically scheduled by a base station in the active state, for a cell in the active state, the second resource may be a resource used to carry the scheduled downlink data; however, for a cell in the dormant state, no downlink data may be scheduled.

It should be noted that, because only a cell in the active state transmits a broadcast channel, and the broadcast channel is transmitted periodically, the method for performing RRM measurement by the UE according to the broadcast channel is the same as the method for performing RRM measurement according to other reference signals.

104. The UE determines a received signal strength indicator RSSI of the target cell according to a total received power on the second resource.

The first resource and the second resource are at different times. Specifically, the first resource and the second resource belong to different OFDM symbols or different timeslots or different subframes or different subframe sets.

Alternatively, optionally, the number of time units included in the second resource is greater than the number of time units included in the first resource, and the time units included in the second resource are inclusive of the time units included in the first resource, where each of the time units may be any one of an OFDM symbol, a timeslot, a subframe, and a subframe set. It may be seen that the second resource carries the first reference signal and second reference information, and that the first reference signal and second reference information are generally at different times, that is, different time units.

105. The UE determines reference signal received quality RSRQ or a signal to interference plus noise ratio SINR of the target cell or both according to the RSRP and RSSI.

It should be noted that, if the target cell is in the active state, the target cell transmits at least one of a DRS, a PSS, an SSS, a CRS, an RCRS, a CSI-RS, a PRS, and a broadcast channel, so that the UE may access or camp on the target cell anytime; if the target cell is in the dormant state, this dormant cell only transmits the first reference signal, that is, a DRS, and the transmission interval of the DRS is much longer than that of the second reference signal to be transmitted when the target cell is in the active state, and is generally an interval of hundreds of subframes or even thousands of subframes. To solve the problem in which the measured RSRQ or SINR is underestimated due to synchronous transmission of a DRS by multiple cells, the RSRP and RSSI are measured on the first resource and the second resource respectively.

Alternatively, if the target cell is in the active state, the target cell transmits at least one of a PSS, an SSS, a CRS, an RCRS, a CSI-RS, a PRS, and a broadcast channel, but does not transmit a DRS. At this time, the UE may identify the cell according to the PSS and SSS, and perform RRM measurement according to the CRS or RCRS. If the target cell is in the dormant state, the target cell may further transmit an RCRS or a CRS, in addition to transmitting a DRS. The transmission interval of the RCRS or CRS may be longer than the transmission interval when the target cell is in the active state. For example, the interval is the same as that of the DRS, and used for the UE to perform RRM measurement, or used together with the DRS to perform RRM measurement.

The first resource and the second resource in this embodiment of the present invention are time resources or frequency resources or both.

In the method for radio resource management measurement according to this embodiment of the present invention, reference signal received quality RSRQ or a signal to interference plus noise ratio SINR of a target cell or both are determined according to a reference signal received power RSRP of the target cell, which is determined by a received power of a first reference signal carried on a first resource, and a received signal strength indicator RSSI of the target cell, which is determined by a total received power on a second resource. In comparison with the prior art in which the RSRQ or SINR of a target cell is measured only according to a CRS or a DRS and an interference environment between neighboring cells in an area is caused to change or vary quickly, the method for radio resource management measurement according to the present invention achieves higher efficiency. In addition, to solve the problem in which the RSRQ or SINR measured by the UE is underestimated in the prior art, a time difference exists between the first resource and the second resource provided by the present invention, so that the RSSI of the target cell does not include the power of a cell in a dormant state (the target cell or a neighboring cell of the target cell or both). Thereby, underestimation of the RSRQ and/or SINR is avoided, and accuracy of radio resource management measurement is further improved.

Figure 3:
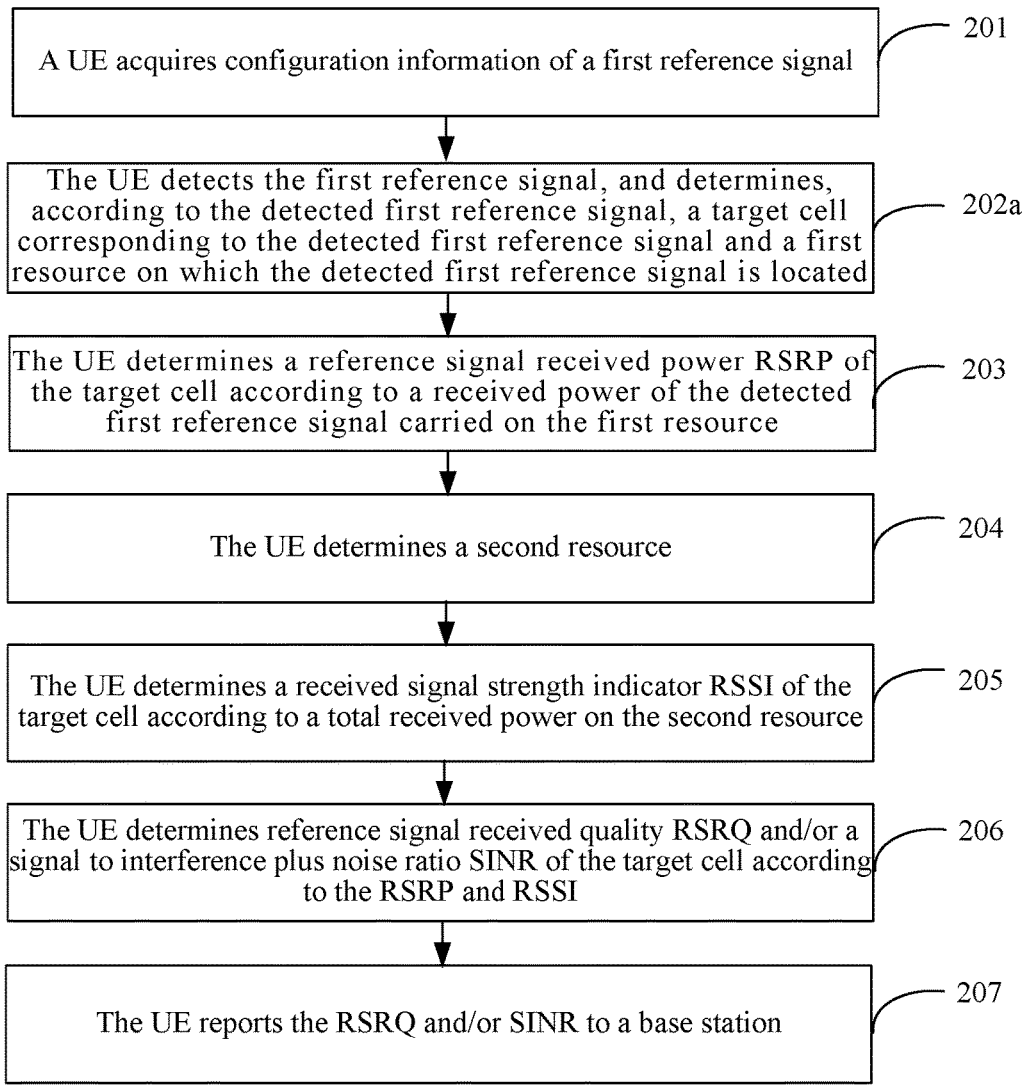
FIG. 3 is a schematic flowchart of yet another method for radio resource management measurement according to an embodiment of the present disclosure.

A method for radio resource management measurement according to an embodiment of the present invention is shown in FIG. 3. The method for radio resource management measurement specifically includes the following steps:

201. A UE acquires configuration information of a first reference signal.

The configuration information includes a candidate sequence of the first reference signal or a candidate time-frequency resource of the first reference signal or both. The candidate time-frequency resource may be a timing, a bandwidth, a time-frequency unit pattern, and the like. Meanwhile, the configuration information may be pre-configured by the UE, or may also be notified by a base station corresponding to a serving cell of the UE.

Specifically, when the serving cell of the UE is a macro cell whose frequency is f1, while a target cell is a small cell whose frequency is f2, the serving cell configures the UE to measure the small cell at the frequency f2. Meanwhile, to reduce measurement complexity and power consumption of the UE, the serving cell notifies some configuration information of the small cell to the UE to assist the UE in cell measurement, for example, notifies the candidate sequence of the first reference signal of the small cell to the UE by using RRC dedicated signaling, so that the UE may detect the first reference signal according to the candidate sequence of the first reference signal, where the candidate sequence includes but is not limited to: a Gold sequence and a Zad-off Chu sequence; and/or notifies, by using RRC (Radio Resource Control) dedicated signaling, the UE of a transmission timing at which the small cell transmits the first reference signal, so that the UE may determine a detection time according to the transmission timing of the first reference signal; and/or notifies a transmission bandwidth of the first reference signal of the small cell to the UE by using RRC dedicated signaling; and/or notifies a time-frequency resource pattern of the first reference signal of the small cell in a resource block to the UE by using RRC dedicated signaling. The serving cell notifies the transmission timing of the first reference signal of the small cell to the UE, mainly because the transmission interval of the first reference signal (for example, a DRS) is generally relatively long (for example, hundreds of subframes). If the UE detects the first reference signal in every subframe, the detection time that the UE spends in detecting the first reference signal is increased, and meanwhile power consumption of the UE is increased. In addition, the transmission timing of the first reference signal of the small cell, which is notified by the serving cell to the UE, may be a specific transmission time, and may also be a radio frame number of the serving cell. Specifically, the serving cell transmits the first reference signal in a position of a radio frame number (for example, 0 or 20 or 40) of the serving cell, and transmits the radio frame number of the serving cell to the UE, so that the UE infers the transmission timing of the first reference signal of the small cell according to a synchronization relationship between the UE and the serving cell. In addition, because the serving cell and the small cell may not be completely synchronized, the foregoing transmission timing may be a rough timing. However, even so, transmitting the transmission timing of the first reference signal may also greatly reduce the detection time and power consumption for the UE to detect the first reference signal.

Optionally, if a third reference signal is used to determine the target cell, it is also necessary to determine in advance configuration information of the third reference signal, including a sequence, a resource, and the like. Assuming that the third reference signal is a PSS and an SSS, it is necessary to determine in advance sequences and resources of the PSS and SSS. Specifically, the configuration information of the third reference signal may be predefined, or may be acquired by receiving a notification from a network side.

202*a*. The UE detects the first reference signal, and determines, according to the detected first reference signal, a target cell corresponding to the detected first reference signal and a first resource on which the detected first reference signal is located.

The first reference signal includes a DRS. The DRS may be designed based on a conventional reference signal, for example, based on at least one of a PRS, a CSI-RS, a CRS, an RCRS, a PSS, and an SSS. Alternatively, some optimization may be performed based on the foregoing conventional reference signal, for example, a sequence of the conventional reference signal remains unchanged, but a time-frequency resource of the conventional reference signal is configured flexibly before the conventional reference signal is used as the DRS.

Optionally, step 202*a* specifically includes the following steps:

202*a*1. The UE detects the first reference signal according to the configuration information of the first reference signal.

202*a*2. The UE determines, according to the configuration information of the detected first reference signal, the target cell corresponding to the detected first reference signal and the first resource on which the detected first reference signal is located.

Specifically, first, after the UE acquires the configuration information of the first reference signal according to the pre-configuration or the notification from the base station corresponding to the serving cell of the UE, the UE may detect the first reference signal according to the configuration information. For example, within a notified transmission timing of the first reference signal and within a notified bandwidth of the frequency of the small cell, the UE detects multiple candidate sequences of the first reference signal, and finally detects a sequence of the first reference signal, for example, by performing matching for these 10 candidate sequences one by one, that is, one of the candidate sequences is matched successfully. Then the UE may determine, according to the actual sequence that is matched successfully and a mapping relationship between the sequence of the first reference signal in the pre-acquired configuration information of the first reference signal and a cell identifier, the cell identifier corresponding to the actual sequence of the first reference signal detected by the UE, that is, identify the target cell. Apparently, the UE may also determine the cell identifier according to the sequence of the first reference signal and a resource element pattern, and further identify the target cell. Next, after identifying the target cell, the UE determines, in a transmission frame of the target cell, a subframe to which the first reference signal belongs, and then determines, in a resource block of the subframe to which the first reference signal belongs, the first resource on which the first reference signal is located, that is, a resource element that carries the detected first reference signal.

It should be noted that, when the UE determines the cell identifier of the target cell and the first resource, the determining may be performed according to a same reference signal (that is, the first reference signal) as shown in step 201*a*, and may also be performed by using respective different reference signals as shown in the following steps 201*b*1 and 201*b*2. That is, steps 201*b*1 and 201*b*2 may replace step 201*a*.

A specific implementation of steps 201*b*1 and 201*b*2 is as follows:

201*b*1. The UE detects a third reference signal, and determines, according to the detected third reference signal, a target cell corresponding to the detected third reference signal.

Further, optionally, step 201b1 further includes the following steps:

a1. The UE acquires configuration information of the third reference signal.

The configuration information includes a candidate sequence of the third reference signal or a candidate time-frequency resource of the third reference signal or both. The candidate time-frequency resource may be a timing, a bandwidth, a time-frequency unit pattern, and the like. Meanwhile, the configuration information may be pre-configured by the UE, or may also be notified by the base station corresponding to the serving cell of the UE.

a2. The UE detects the third reference signal according to the configuration information of the third reference signal.

a3. The UE determines, according to the configuration information of the detected third reference signal, the target cell corresponding to the detected third reference signal.

201b2. The UE detects a first reference signal, and determines, according to the detected first reference signal, a first resource on which the detected first reference signal is located.

Further, optionally, step 201b2 further includes the following steps:

b1. The UE detects the first reference signal according to the configuration information of the first reference signal.

b2. The UE determines, according to the detected first reference signal, the first resource on which the detected first reference signal is located.

The third reference signal in steps 201b1 and 201b2 may be a synchronization signal, that is, a PSS or an SSS or a combination thereof. The synchronization signal may also be regarded as a DRS or a part of a DRS. At this time, the UE may determine the cell identifier of the target cell according to the detected PSS or SSS or both. Correspondingly, the first reference signal used for the UE to determine the first resource in step 201b2 may be at least one of a PRS, a CSI-RS, a CRS, and an RCRS. The first reference signal may be regarded as a DRS or another part of a DRS, and the first reference signal is used for RRM measurement of the target cell. For details, reference may be made to the following steps:

203. The UE determines a reference signal received power RSRP of the target cell according to a received power of the detected first reference signal carried on the first resource.

Specifically, the power of the first reference signal on the first resource is averaged. For example, if the first reference signal is carried on 10 resource elements, an average received power of the first reference signal on these 10 resource elements is used as an RSRP.

204. The UE determines a second resource.

Specifically, after determining the first resource of the first reference signal of the target cell, the UE further needs to determine the second resource. The second resource refers to all or a part of resource elements in an entire OFDM symbol in which second reference information of the target cell is located, and may also include a timeslot, a subframe, a subframe set, or a radio frame in which the OFDM symbol is located. The second reference information includes at least one of a CSI-RS, a CRS, an RCRS, a PSS, an SSS, a PRS, and a broadcast channel. Specifically, when the target cell is in an active state, the target cell transmits at least the second reference information on the second resource; and when the target cell is in a dormant state, because the target cell does not transmit the second reference information, that is, only the first reference signal exists in a transmission frame of the target cell, the target cell transmits the detected first reference signal on the first resource, and does not transmit the second reference information on the second resource. However, if the target cell changes from the dormant state to the active state, the second resource carries the second reference information. In addition, the second reference information may also be downlink data. Because the downlink data is dynamically scheduled by a base station in the active state, for a cell in the active state, the second resource may be a resource used to carry the scheduled downlink data; however, for a cell in the dormant state, no downlink data may be scheduled. The foregoing feature of the second resource regarding whether or not to carry the second reference information is also applicable to a neighboring cell of the target cell.

Optionally, the second resource is only required to not carry the first reference signal, that is, the second resource is any resource that does not carry the first reference signal, and may or may not carry the second reference information. If the second reference information is not carried, the power on the second resource is determined according to a dynamically scheduled data channel, that is, if data is scheduled, there is a power, or otherwise, there may be no power. In this way, an impact of interference caused by a data channel may be reflected more accurately. Apparently, if the second resource carries the second reference information, the second reference information does not depend on dynamic data scheduling, and the second reference information may be transmitted providing that the target cell is in the active state. In this case, the measured interference may not accurately reflect the interference caused by a data channel, but the measured interference is stable and does not vary greatly, so that the network side can make use of the measurement result from the UE, for example, add or remove a cell or perform a handover for the UE.

It should be noted that, because only a cell in the active state transmits a broadcast channel, and the broadcast channel is transmitted periodically, the method for performing RRM measurement by the UE according to the broadcast channel is the same as the method for performing RRM measurement according to other reference signals.

Optionally, step 204 specifically includes the following:

204a. The UE determines the second resource according to the first resource and a resource offset.

The resource offset includes a time-domain offset or a frequency offset or both, and the resource offset is pre-configured by the UE or is notified by the base station corresponding to the serving cell of the UE by using auxiliary RRC signaling. Specifically, the UE may determine the second resource according to the resource offset between the second resource and the first resource (for example, a spacing of N OFDM symbols exists between an OFDM symbol of the second resource and an OFDM symbol of the first resource, or a spacing of N subframes exists between a subframe of the second resource and a subframe of the first resource). In this way, after determining the first resource, the UE may determine a time-domain position of the second resource according to the resource offset. A determined frequency position of the second resource may be pre-configured, or may be the same as a frequency position of the first resource, or may have an offset from frequency of the first resource, which is not specifically limited herein.

205. The UE determines a received signal strength indicator RSSI of the target cell according to a total received power on the second resource.

Specifically, the UE measures a total received power in an OFDM symbol in which the second reference information is located, where the total received power includes received powers of all signals in the OFDM symbol, including a received power of the target cell, a power of the neighboring cell of the target cell in the OFDM symbol, noise, and the like. The UE does not distinguish different signals in the OFDM symbol, but only measures received powers in the OFDM symbol, and uses an average value of the total received powers in multiple OFDM symbols as the RSSI of the target cell. Apparently, averaging may also not be performed herein, and a specific calculation manner is not limited herein. It is only required that the UE determine the RSSI of the target cell according to the total received power in the OFDM symbol. It is even allowed to count the received power in the OFDM symbol into received powers of 14 OFDM symbols of an entire subframe or more subframes, and use an average of received powers of these 14 OFDM symbols as the RSSI of the target cell.

The first resource and the second resource are at different times. Specifically, the first resource and the second resource belong to different OFDM symbols or different timeslots or different subframes or different subframe sets, providing that the first resource and the second resource are different in the time domain.

Alternatively, optionally, the number of time units included in the second resource is greater than the number of time units included in the first resource, and the time units included in the second resource are inclusive of the time units included in the first resource, where each of the time units may be any one of an OFDM symbol, a timeslot, a subframe, and a subframe set. It may be seen that the second resource carries the first reference signal and second reference information, and that the first reference signal and second reference information are generally at different times, that is, different time units.

Specifically, an example of the time units being OFDM symbols is used for description. It is assumed that the first resource is OFDM symbol 0 of a subframe, where the OFDM symbol 0 carries the first reference signal, and meanwhile it is also assumed that all the 14 OFDM symbols included in the subframe are the second resource, and the second reference information is OFDM symbol 1 among the 14 OFDM symbols in the subframe. It may be seen that at this time, the number of OFDM symbols in the second resource is greater than the number of OFDM symbols in the first resource and that the OFDM symbol 0 included in the first resource is among the 14 OFDM symbols included in the second resource, and meanwhile it may also be seen that the OFDM symbols in which the second reference information and the first reference signal are located are different. Apparently, the second reference information and the first reference signal may also be located in a same OFDM symbol, that is, they occupy different frequency-domain resource elements in the same OFDM symbol. However, they generally occupy different time units.

In the implementation method in which the first resource and the second resource occupy different times, the first reference signal on the first resource may be used to measure the RSRP, and the second reference information on the second resource may be used to measure the RSSI. In this way, a case in which the RSSI includes the power of a DRS of a cell in the dormant state may be avoided. In comparison with the implementation method in which the first resource and the second resource occupy different times, the implementation method in which the second resource includes the first resource and the number of time units included in the second resource is greater than the number of time units included in the first resource may also solve the problem of the RSRQ being underestimated. Specifically, although the RSSI measured on the second resource includes the power of the first reference signal on the first resource, that is, includes the received power of the DRS of the cell in the dormant state, the number of time units included in the second resource is greater than the number of time units included in the first resource, which may achieve an effect of averaging the RSSI. For example, the power of a DRS in 1 OFDM symbol included in the RSSI is counted into powers of 14 OFDM symbols in the entire second resource and an average of powers in these 14 OFDM symbols is used as the RSSI, which achieves an effect of smoothing the underestimated RSRQ or SINR. More importantly, the second resource further carries second reference information, where the second reference information is information that is transmitted only by a cell in the active state, and this makes the RSRQ or SINR measurement more accurate than in the case of the second resource carrying only the first reference signal. Specifically, if the second resource carries only the first reference signal and all or a majority of cells around the UE are in the active state, a measurement result obtained after smoothing processing is performed for DRSs of the cells in the active state is overestimated when compared with an actual result. However, if the second resource carries not only the first reference signal, but also the second reference information that needs to be transmitted when a cell is in the active state and will not be transmitted when a cell is in the dormant state, the problem of the smoothed RSRQ or SINR being overestimated may be solved. In conclusion, when a majority of cells are in the dormant state, the implementation method performs smoothing processing for the measurement result to solve the problem of the RSRQ or SINR being underestimated; and when a majority of cells are in the active state, the method in which the second resource carries the second reference information is used to solve the problem of the RSRQ or SINR being overestimated. Thereby, the RRM measurement in each of the foregoing scenarios is accurate on the whole.

It should be noted that, specifically two implementation manners are included when the UE determines the RSSI of the target cell according to the total received power on the second resource. A first implementation manner is: the UE directly uses the total received power on the second resource or the total received power multiplied by a coefficient as the RSSI. A second implementation manner is: the UE adds together the received powers in the time units occupied by the first reference signal and the received powers in the time units occupied by the second reference information, and then divides the sum by the total number of time units included in the entire second resource to perform averaging, and finally obtains the RSSI.

206. The UE determines reference signal received quality RSRQ or a signal to interference plus noise ratio SINR of the target cell or both according to the RSRP and RSSI.

Specifically, after determining the RSRP and RSSI, the UE may further determine the RSRQ or SINR according to a ratio of the RSRP to the RSSI, that is, the RSRP divided by the RSSI. The UE may directly use the ratio as the RSRQ or SINR, and may also use the ratio multiplied by a coefficient as the RSRQ or SINR. The coefficient may be determined according to a current measurement bandwidth, and may also be determined according to an averaged parameter. When the coefficient is determined according to the current measurement bandwidth, a wider measurement bandwidth means a greater coefficient; or when the coefficient is determined according to the averaged parameter, the averaged parameter may be a result of averaging in which the received power in the symbol in which the RSRP or RSSI is measured is divided by the 14 OFDM symbols of an entire subframe, and may also be a result of averaging in which the received power in the symbol in which the RSRP or RSSI is measured is divided by N*14 OFDM symbols of N subframes. It should be noted that, because the RSSI is a denominator for calculating the RSRQ or SINR, and the RSSI of the target cell does not include the power of the cell in the dormant state, the RSRQ or SINR finally determined according to the present invention is not underestimated as it would in the case of counting the power of the DRS of the cell in the dormant state into the RSSI.

Further, for SINR measurement, the second resource may not only be an OFDM symbol in which the second reference information is located, but also may be a timeslot in which the second reference information is located, and may further be resource elements at a part of frequencies in a subframe or subframe set in which the second reference information is located. For example, assuming that the second resource is an OFDM symbol in which an RCRS is located, different cells occupy different frequency-domain positions of the OFDM in a same measurement frequency band (for example, different subcarriers in the OFDM symbol in which the RCRS is located), and therefore, for interference or interference plus noise of the target cell, it is only necessary to measure a received power of a subcarrier corresponding to the target cell in the OFDM symbol. However, because the target cell does not transmit a signal in the position of the subcarrier, the UE measures, in this position, interference caused by another cell to the target cell. In addition, because the target cell is in the dormant state, and the second resource does not carry the second reference information of the target cell, the interference or interference plus noise which is measured by the UE does not include the power of the cell in the dormant state. Therefore, the SINR finally obtained by the UE is not underestimated.

Optionally, step 206 specifically includes the following: If a transmit power of the target cell on the second resource is not 0, the UE determines the RSRQ of the target cell according to the RSRP and RSSI; and/or if a transmit power of the target cell on the second resource is 0, the UE determines the SINR of the target cell according to the RSRP and RSSI.

Specifically, if the transmit power of the target cell on the second resource is not 0, the UE determines the RSRQ of the first cell according to the RSRP and RSSI, because at this time, the power of the target cell in the second resource is not 0, that is, the power of the second reference information carried on the second resource is not 0. If the transmit power of the target cell on the second resource is 0, the UE determines the SINR of the target cell according to the RSRP and RSSI, because at this time, the power of the target cell on the second resource is 0, that is, the second resource does not carry the second reference information.

Optionally, the UE may further determine the RSRQ or SINR according to the ratio of the measured RSRP to the measured RSRP+RSSI, that is, RSRP/(RSRP+RSSI). For example, if the target cell is in the dormant state, the RSSI does not include the signal of the target cell, and therefore, the RSRP may be added to the denominator, and a measured value similar to the RSRQ is obtained. Apparently, it may be seen that, the RSRP/RSSI and RSRP/(RSRP+RSSI) may be converted mutually, that is, the UE may also directly report the former to the base station, and the base station obtains the RSRP/(RSRP+RSSI) by calculation according to the reported RSRP/RSSI. Apparently, the UE may also directly report the RSRP/(RSRP+RSSI).

Further, if enabling/disabling of a small cell or a state transition thereof is transparent to the UE, that is, when the UE performs RRM measurement for the small cell, the UE is not aware whether the small cell is in the active state or dormant state, then if the target cell is in the active state, the measurement result is the RSRQ; and if the target cell is in the dormant state, the measurement result is the SINR. In this way, if the UE averages measurement results of multiple DRSs, that is, if the UE performs averaging processing for the results of the RSRQ and SINR, such processing occurs during a state transition of the target cell, and causes the measurement result to be inaccurate. That is, the measurement result can neither accurately reflect the RSRQ, nor accurately reflect the SINR, but is an average value of the two, and an impact may be caused when the base station subsequently uses the result reported by the UE.

A method for further solving the foregoing problem may be as follows: The UE determines multiple time windows. A start point and length of each time window may be predefined or may be notified by the base station. Then the UE is only allowed to perform averaging processing for RRM measurement results in each time window. Correspondingly, the target cell only performs state transitions at boundaries of the multiple windows, thereby ensuring that a result obtained by the UE after measurement averaging in each window is either the RSRQ or the SINR, so that the measurement of both is accurate.

Optionally, after step 206, the following is further included:

207a. The UE reports the RSRQ to the base station, so that the base station determines, according to the RSRQ reported by the UE, whether to switch the target cell from the dormant state to the active state, and/or determines, according to the RSRQ reported by the UE, whether to configure the target cell for the UE.

Alternatively,

207b. The UE reports the SINR to the base station, so that the base station determines, according to the SINR reported by the UE, whether to switch the target cell from the dormant state to the active state, and/or determines, according to the SINR reported by the UE, whether to configure the target cell for the UE.

Alternatively,

207c. The UE reports the RSRQ and SINR to the base station, so that the base station determines, according to the RSRQ and SINR reported by the UE, whether to switch the target cell from the dormant state to the active state, and/or determines, according to the RSRQ and SINR reported by the UE, whether to configure the target cell for the UE.

Specifically, after the UE finally obtains the RSRQ or SINR or both by measurement in different application scenarios (that is, only the RSRQ is obtained by measurement, or only the SINR is obtained by measurement, or both the RSRQ and the SINR are obtained by measurement), the UE may report the measurement result of the target cell to the base station corresponding to the serving cell of the UE (for example, the macro cell). After the base station receives the RSRQ or SINR or both, the base station determines, according to the measurement result reported by the UE, whether to configure the target cell corresponding to the measurement result for the UE. If the target cell is in the dormant state, the base station may further determine whether to switch the target cell from the dormant state to the active state, and configure the target cell for the UE.

It should be noted that, if the target cell is in the active state, the target cell transmits at least one of a DRS, a PSS, an SSS, a CRS, an RCRS, a CSI-RS, a PRS, and a broadcast channel, so that the UE may access or camp on the target cell anytime; if the target cell is in the dormant state, this dormant cell only transmits the first reference signal, that is, a DRS, and the transmission interval of the DRS is much longer than that of the second reference signal to be transmitted when the target cell is in the active state, and is generally an interval of hundreds of subframes or even thousands of subframes. To solve the problem in which the measured RSRQ or SINR is underestimated due to synchronous transmission of a DRS by multiple cells, the RSRP and RSSI are respectively measured on the first resource and the second resource.

Alternatively, if the target cell is in the active state, the target cell transmits at least one of a PSS, an SSS, a CRS, an RCRS, a CSI-RS, a PRS, and a broadcast channel, but does not transmit a DRS. At this time, the UE may identify the cell according to the PSS and SSS, and perform RRM measurement according to the CRS or RCRS. If the target cell is in the dormant state, the target cell may further transmit an RCRS or a CRS, in addition to transmitting a DRS. The transmission interval of the RCRS or CRS may be longer than the transmission interval when the target cell is in the active state. For example, the interval is the same as that of the DRS, and used for the UE to perform RRM measurement, or used together with the DRS to perform RRM measurement.

In the method for radio resource management measurement according to this embodiment of the present invention, reference signal received quality RSRQ or a signal to interference plus noise ratio SINR of a target cell or both are determined according to a reference signal received power RSRP of the target cell, which is determined by a received power of a first reference signal carried on a first resource, and a received signal strength indicator RSSI of the target cell, which is determined by a total received power on a second resource. In comparison with the prior art in which the RSRQ or SINR of a target cell is measured only according to a CRS or a DRS and an interference environment between neighboring cells in an area is caused to change or vary quickly, the method for radio resource management measurement according to the present invention achieves higher efficiency. In addition, to solve the problem in which the RSRQ or SINR measured by the UE is underestimated in the prior art, a time difference exists between the first resource and the second resource provided by the present invention, so that the RSSI of the target cell does not include the power of a cell in a dormant state (the target cell or a neighboring cell of the target cell or both). Thereby, underestimation of the RSRQ and/or SINR is avoided, and accuracy of radio resource management measurement is further improved.

Figure 4:
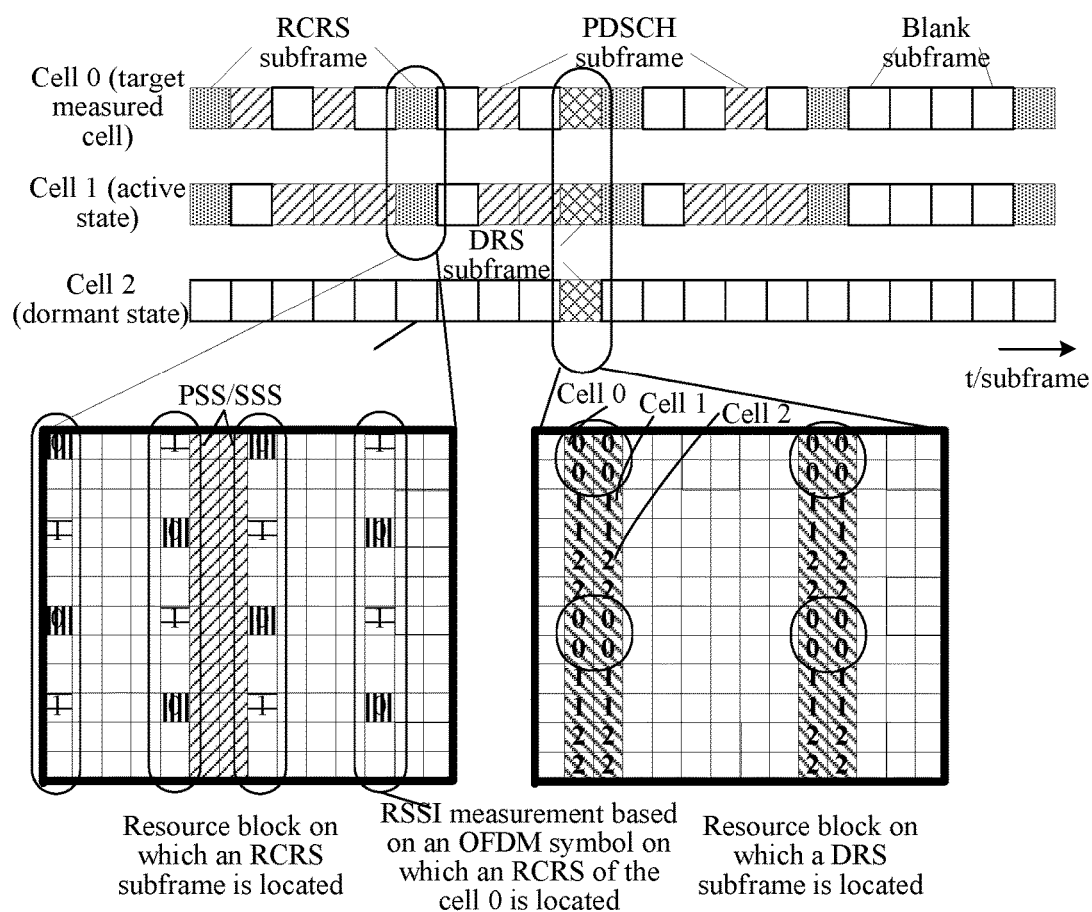
FIG. 4 is a schematic diagram of transmission frames and subframes of resource blocks in these transmission frames of a target cell and a neighboring cell of the target cell according to an embodiment of the present disclosure.
Figure 5:
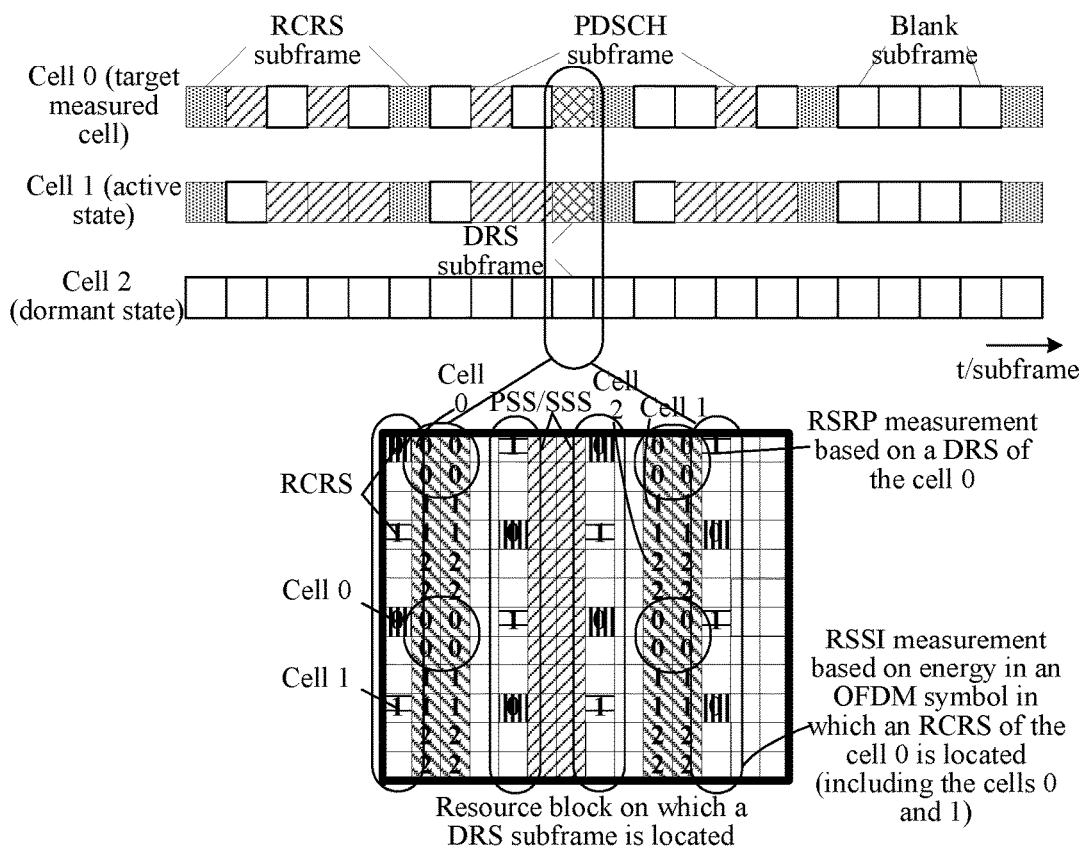
FIG. 5 is another schematic diagram of transmission frames and subframes of resource blocks in these transmission frames of a target cell and a neighboring cell of the target cell according to an embodiment of the present disclosure.
Figure 6:
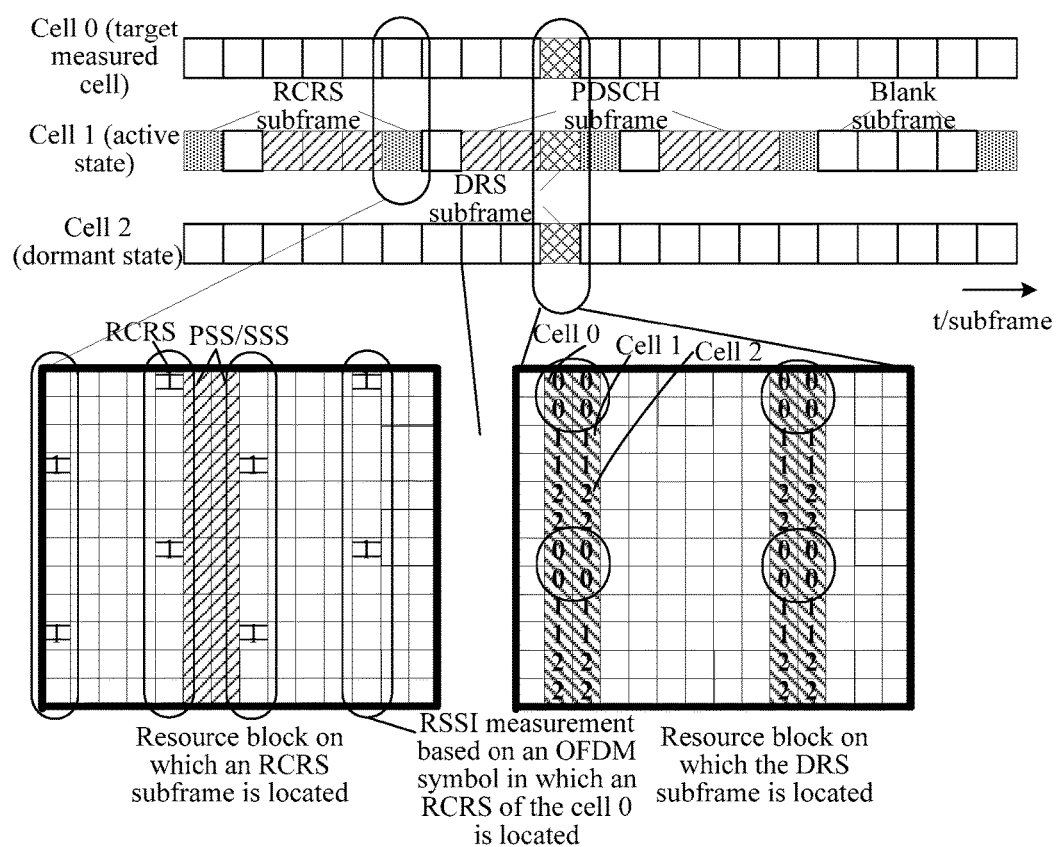
FIG. 6 is yet another schematic diagram of transmission frames and subframes of resource blocks in these transmission frames of a target cell and a neighboring cell of the target cell according to an embodiment of the present disclosure.

Specifically, a method for radio resource management measurement in three application scenarios is provided herein. In the example of FIG. 4 through FIG. 6, a first reference signal is a DRS, second reference information is RCRS, a target cell is cell 0, and neighboring cells are cell 1 and cell 2.

In a first application scenario (that is, a target cell is in an active state, and a DRS and an RCRS of the target cell are located in different subframes):

First, after a UE detects the cell 0 according to pre-acquired configuration information of the DRS, the UE determines a first resource on which the DRS of the cell 0 is located, that is, a total of 16 REs in 4 OFDM symbols shown in FIG. 4, and then measures an average received power of the DRS on the 16 REs, and uses the average received power as an RSRP of the cell 0. Herein it should be noted that, the 16 REs on which the DRS of the cell 0 is located may further carry interference information and noise transmitted on the same resource by another cell. However, herein it is only necessary to measure the average received power of the DRS of the cell 0 on the 16 REs, and the interference power and noise power are not counted into the RSRP.

Then, the UE determines a second resource according to a preset resource offset between the first resource and the second resource and a position of the first resource in a resource block of a subframe. Because the cell 0 is in the active state, the second resource refers to all resources in an OFDM symbol in which the RCRS is located. As may be seen from the positions of the first resource and second resource in FIG. 4, a spacing of 4 subframes exists between the second resource and the first resource, and the second resource refers to the REs in the 4 columns of OFDM symbols in which the RCRS is located. After the UE determines the position of the second resource, the UE measures a total received power in the OFDM symbol in which the RCRS is located, where the total received power includes received powers of all signals in the OFDM symbol, and uses an average value of the received powers in multiple OFDM symbols as an RSSI of the cell 0. Apparently, averaging may also not be performed, which is not limited herein.

As shown in FIG. 4, the cell 0, which is a measured cell, is in the active state, and the active state means that at least a second reference signal is transmitted in the cell 0, where the second reference signal is at least one of a DRS, a CRS, an RCRS, a PSS, an SSS, and a CSI-RS, and may also be reference information such as a broadcast channel or a data channel; the cell 2 is in a dormant state, that is, a DRS or only a DRS is transmitted in the cell 2, and therefore, a transmit power on the second resource is 0; for another neighboring cell 1 in the active state, a second reference signal or reference information such as a data channel or a broadcast channel is also transmitted in the cell 1, and the power of the second reference information causes interference to the target cell. It may be seen that, the second resource is different from the first resource in which the DRS is transmitted. Therefore, the RSSI obtained by measurement does not include the power of the cell 2, that is, the power of the cell in the dormant state is not counted into the RSSI of the measured cell, but the power of the neighboring cell in the active state may be counted into the RSSI as an interference power.

Finally, after measuring the RSRP and RSSI, the UE may further determine the RSRQ or SINR according to a ratio of the RSRP to the RSSI, that is, the RSRP divided by the RSSI. At this time, because the cell 0 is in the active state, the transmit power of the cell 0 on the second resource is not 0, that is, the transmit power of the RCRS on the second resource is not 0. At this time, the UE calculates the RSRQ according to the RSRP and RSSI.

In the method for radio resource management measurement according to this embodiment of the present invention, reference signal received quality RSRQ of a target cell is determined according to a reference signal received power RSRP of the target cell, which is determined by a received power of a first reference signal carried on a first resource, and a received signal strength indicator RSSI of the target cell, which is determined by a total received power on a second resource. In comparison with the prior art in which the RSRQ or SINR of a target cell is measured only according to a CRS or a DRS and an interference environment between neighboring cells in an area is caused to change or vary quickly, the method for radio resource management measurement according to the present invention achieves higher efficiency. In addition, to solve the problem in which the RSRQ or SINR measured by the UE is underestimated in the prior art, a time difference exists between the first resource and the second resource provided by the present invention, so that the RSSI of the target cell does not include the power of a cell in a dormant state (the target cell or a neighboring cell of the target cell or both). Thereby, underestimation of the RSRQ is avoided, and accuracy of radio resource management measurement is further improved.

In a second application scenario (that is, a target cell is in an active state, and a DRS and an RCRS of the target cell are located in a same subframe):

First, after a UE detects the cell 0 according to pre-acquired configuration information of the DRS, the UE determines a first resource on which the DRS of the cell 0 is located, that is, a total of 16 REs in 4 OFDM symbols shown in FIG. 5, and then measures an average received power of the DRS on the 16 REs, and uses the average received power as an RSRP of the cell 0. Apparently, the UE may measure more DRS subframes, and thereby measure the RSRP according to more REs of the DRS. If more REs are used for measurement, the RSRP obtained by measurement is more accurate; the number of REs to use is not limited herein. In addition, it should also be noted that, the 16 REs on which the DRS of the cell 0 is located may further carry interference information and noise transmitted on the same resource by another cell. However, herein it is only necessary to measure the average received power of the DRS of the cell 0 on the 16 REs, and the interference power and noise power are not counted into the RSRP.

Then, the UE determines a second resource according to a preset resource offset between the first resource and the second resource and a position of the first resource in a resource block of a subframe. Because the cell 0 is in the active state, the second resource refers to all resources in an OFDM symbol in which the RCRS is located. As shown in FIG. 5, it may be seen that the second resource and the first resource are located in the same subframe, that is, the DRS is transmitted in an RCRS subframe, and a fixed positional relationship exists between an OFDM symbol of the DRS and an OFDM symbol of the RCRS. Then the UE determines a symbol in which the DRS is located, and may further determine an OFDM symbol of the second resource, that is, a symbol in which the RCRS is located. After the UE determines the position of the second resource, the UE measures a total received power in the OFDM symbol in which the RCRS is located, where the total received power includes received powers of all signals in the OFDM symbol, and uses an average value of the received powers in multiple OFDM symbols as an RSSI of the cell 0. Apparently, averaging may also not be performed, which is not limited herein.

As shown in FIG. 5, the cell 0, which is a measured cell, is in the active state, and the active state means that at least a second reference signal is transmitted in the cell 0, where the second reference signal is at least one of a DRS, a CRS, an RCRS, a PSS, an SSS, and a CSI-RS, and may also be reference information such as a broadcast channel or a data channel; the cell 2 is in a dormant state, that is, a DRS or only a DRS is transmitted in the cell 2, and therefore, a transmit power on the second resource is 0; for another neighboring cell 1 in the active state, a second reference signal or reference information such as a data channel or a broadcast channel is also transmitted in the cell 1, and the power of the second reference information causes interference to the target cell. It may be seen that, the second resource is different from the first resource in which the DRS is transmitted. Therefore, the RSSI obtained by measurement does not include the power of the cell 2, that is, the power of the cell in the dormant state is not counted into the RSSI of the measured cell, but the power of the neighboring cell in the active state may be counted into the RSSI as an interference power.

Finally, after measuring the RSRP and RSSI, the UE may further determine the RSRQ or SINR according to a ratio of the RSRP to the RSSI, that is, the RSRP divided by the RSSI. At this time, because the cell 0 is in the active state, the transmit power of the cell 0 on the second resource is not 0, that is, the transmit power of the RCRS on the second resource is not 0. At this time, the UE calculates the RSRQ according to the RSRP and RSSI.

In the method for radio resource management measurement according to this embodiment of the present invention, reference signal received quality RSRQ of a target cell is determined according to a reference signal received power RSRP of the target cell, which is determined by a received power of a first reference signal carried on a first resource, and a received signal strength indicator RSSI of the target cell, which is determined by a total received power on a second resource. In comparison with the prior art in which the RSRQ or SINR of a target cell is measured only according to a CRS or a DRS and an interference environment between neighboring cells in an area is caused to change or vary quickly, the method for radio resource management measurement according to the present invention achieves higher efficiency. In addition, to solve the problem in which the RSRQ or SINR measured by the UE is underestimated in the prior art, a time difference exists between the first resource and the second resource provided by the present invention, so that the RSSI of the target cell does not include the power of a cell in a dormant state (the target cell or a neighboring cell of the target cell or both). Thereby, underestimation of the RSRQ is avoided, and accuracy of radio resource management measurement is further improved.

In a third application scenario (that is, a target cell is in an active state, a DRS and an RCRS of the target cell are located in a same subframe, the number of time units included in a second resource is greater than the number of time units included in a first resource, and the time units included in the second resource are inclusive of the time units included in the first resource, where the time units are OFDM symbols):

This embodiment is based on the embodiment in FIG. 5. First, a UE measures an RSRP. The method for measuring the RSRP by the UE is the same as the embodiment shown in FIG. 5, and details are not described herein again.

Next, the UE obtains an RSSI based on a total received power on the second resource. As shown in FIG. 5, at this time, the second resource is a subframe formed by 14 OFDM symbols, and the first resource on which a first reference signal is located is a part of OFDM symbols in the second resource. At this time, the RSSI is smoothed in the entire subframe. This solves the problem of the underestimated RSRQ or SINR which occurs when many cells are in a dormant state. On the other hand, if the second resource carries only the first reference signal, that is, the DRS, when many cells are in the active state, powers of signals other than the DRSs of the cells in the active state are not taken into account, and therefore, the problem of the RSRQ or SINR being overestimated is caused. At this time, in addition to the first reference signal (for example, a CSI-RS as shown in FIG. 5), the second resource further carries second reference information (for example, as shown in FIG. 5, an RCRS or a CRS that is transmitted only by a cell in the active state). Thereby, the problem of measurement overestimation after smoothing may be solved, measurement is more accurate, and the method for radio resource management measurement achieves higher efficiency. One manner of practicing the smoothing method is to directly use the total received power in all the 14 symbols of the subframe in which the second resource is located or the total received power multiplied by a coefficient as the RSSI. Another manner is to add together the received powers in the time units (that is, a part of OFDM symbols) occupied by the first reference signal and the received powers in the time units (another part of OFDM symbols, which do not overlap the OFDM symbols occupied by the first reference signal) occupied by the second reference information, and then divide the sum by the total number of time units included in the entire second resource (that is, the total of 14 OFDM symbols) to perform averaging, and finally obtain the RSSI.

In the method for radio resource management measurement according to this embodiment of the present invention, reference signal received quality RSRQ of a target cell is determined according to a reference signal received power RSRP of the target cell, which is determined by a received power of a first reference signal carried on a first resource, and a received signal strength indicator RSSI of the target cell, which is determined by a total received power on a second resource. In comparison with the prior art in which the RSRQ or SINR of a target cell is measured only according to a CRS or a DRS and an interference environment between neighboring cells in an area is caused to change or vary quickly, the method for radio resource management measurement according to the present invention achieves higher efficiency. In addition, to solve the problem in which the RSRQ or SINR measured by the UE is underestimated in the prior art, the present invention provides a method for performing smoothing processing for measurement results in multiple time units, which solves the problem of the RSRQ or SINR being underestimated when many cells are in a dormant state, and further solves the problem of the RSRQ or SINR being overestimated when many cells are in an active state, and thereby further improves accuracy of radio resource management measurement.

In a fourth application scenario (that is, a target cell is in a dormant state, and a DRS and an RCRS of the target cell are located in different subframes):

First, after a UE detects the cell 0 according to pre-acquired configuration information of the DRS, the UE determines a first resource on which the DRS of the cell 0 is located, that is, a total of 16 REs in 4 OFDM symbols shown in FIG. 6, and then measures an average received power of the DRS on the 16 REs, and uses the average received power as an RSRP of the cell 0. Apparently, the UE may measure more DRS subframes, and thereby measure the RSRP according to more REs of the DRS. If more REs are used for measurement, the RSRP obtained by measurement is more accurate; the number of REs to use is not limited herein. In addition, it should also be noted that, the 16 REs on which the DRS of the cell 0 is located may further carry interference information and noise transmitted in the same resource by another cell. However, herein it is only necessary to measure the average received power of the DRS of the cell 0 on the 16 REs, and the interference power and noise power are not counted into the RSRP.

Then a second resource is determined according to a preset resource offset between the first resource and the second resource and a position of the first resource in a resource block of a subframe. It should be noted that, although the cell 0 is in the dormant state and does not transmit an RCRS, the second resource used to carry the RCRS does indeed exist. However, no RCRS is carried on the second resource. Therefore, the UE may still acquire the position of the second resource according to the position of the first resource and the preset resource offset between the first resource and the second resource. After the UE determines the second resource, because the cell 0, which is a measured cell, and a cell 2, which is a neighboring cell, are both in the dormant state at this time, received powers of the cell 0 and cell 2 are not counted into an RSSI of the cell 0. Therefore, the RSSI of the cell 0 includes only the received power of the neighboring cell 1.

Finally, after measuring the RSRP and RSSI, the UE may further determine the RSRQ or SINR according to a ratio of the RSRP to the RSSI, that is, the RSRP divided by the RSSI. At this time, because the cell 0 is in the dormant state, the transmit power of the cell 0 on the second resource is 0, that is, no RCRS is transmitted on the second resource, and apparently, other second reference information is not transmitted on the second resource, either. At this time, the UE calculates the SINR according to the RSRP and RSSI.

In the method for radio resource management measurement according to this embodiment of the present invention, reference signal received quality RSRQ or a signal to interference plus noise ratio SINR of a target cell or both are determined according to a reference signal received power RSRP of the target cell, which is determined by a received power of a first reference signal carried on a first resource, and a received signal strength indicator RSSI of the target cell, which is determined by a total received power on a second resource. In comparison with the prior art in which the SINR of a target cell is measured only according to a CRS or a DRS and an interference environment between neighboring cells in an area is caused to change or vary quickly, the method for radio resource management measurement according to the present invention achieves higher efficiency. In addition, to solve the problem in which the RSRQ or SINR measured by the UE is underestimated in the prior art, a time difference exists between the first resource and the second resource provided by the present invention, so that the RSSI of the target cell does not include the power of a cell in a dormant state (the target cell or a neighboring cell of the target cell or both). Thereby, underestimation of the SINR is avoided, and accuracy of radio resource management measurement is further improved.

Figure 7:
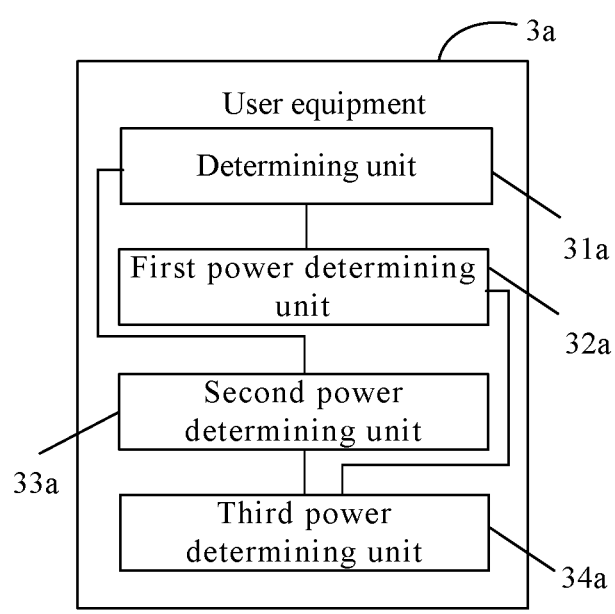
FIG. 7 is a schematic structural diagram of a user equipment according to an embodiment of the present disclosure.

An embodiment of the present invention provides a user equipment. The user equipment is used to implement the foregoing method for radio resource management measurement. As shown in FIG. 7, the user equipment 3a includes: a determining unit 31a, a first power determining unit 32a, a second power determining unit 33a, and a third power determining unit 34a.

The determining unit 31a is configured to detect a first reference signal, and determine, according to the detected first reference signal, a target cell corresponding to the detected first reference signal and a first resource on which the detected first reference signal is located.

The first power determining unit 32a is configured to determine a reference signal received power RSRP of the target cell according to a received power of the detected first reference signal carried on the first resource.

The determining unit 31a is further configured to determine a second resource.

The first resource and the second resource are at different times.

The second resource is used to carry second reference information when the target cell is in an active state, or the second resource is used to not carry second reference information when the target cell is in a dormant state and used to carry the second reference information when the target cell changes from the dormant state to the active state. The foregoing feature of the second resource regarding whether or not to carry the second reference information is also applicable to a neighboring cell of the target cell.

The second power determining unit 33a is configured to determine a received signal strength indicator RSSI of the target cell according to a total received power on the second resource.

The third power determining unit 34a is configured to determine reference signal received quality RSRQ or a signal to interference plus noise ratio SINR of the target cell according to the RSRP and RSSI.

The user equipment provided by this embodiment of the present invention determines reference signal received quality RSRQ or a signal to interference plus noise ratio SINR of a target cell or both according to a reference signal received power RSRP of the target cell, which is determined by a received power of a first reference signal carried on a first resource, and a received signal strength indicator RSSI of the target cell, which is determined by a total received power on a second resource. In comparison with the prior art in which the RSRQ or SINR of a target cell is measured only according to a CRS or a DRS and an interference environment between neighboring cells in an area is caused to change or vary quickly, the method for radio resource management measurement according to the present invention achieves higher efficiency. In addition, to solve the problem in which the RSRQ or SINR measured by the UE is underestimated in the prior art, a time difference exists between the first resource and the second resource provided by the present invention, so that the RSSI of the target cell does not include the power of a cell in a dormant state (the target cell or a neighboring cell of the target cell or both). Thereby, underestimation of the RSRQ and/or SINR is avoided, and accuracy of radio resource management measurement is further improved.

Figure 8:
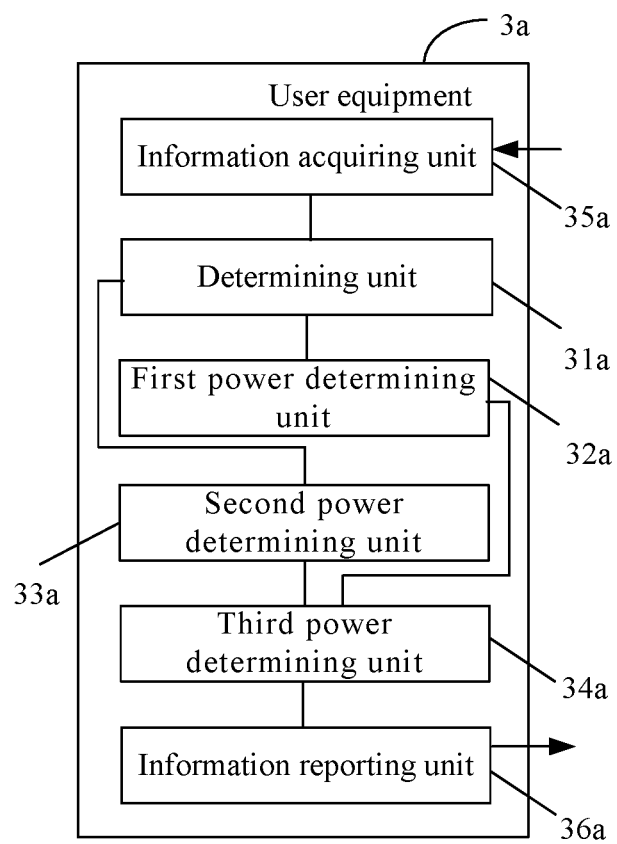
FIG. 8 is a schematic structural diagram of another user equipment according to an embodiment of the present disclosure.

Optionally, as shown in FIG. 8, the user equipment 3a further includes: an information acquiring unit 35a.

The information acquiring unit 35a is configured to acquire configuration information of the first reference signal.

The configuration information includes a candidate sequence of the first reference signal or a candidate time-frequency resource of the first reference signal or both.

The determining unit 31a is specifically configured to: detect the first reference signal according to the configuration information of the first reference signal; and determine, according to the configuration information of the detected first reference signal, the target cell corresponding to the detected first reference signal and the first resource on which the detected first reference signal is located.

Optionally, the determining unit 31a is specifically configured to determine the second resource according to the first resource and a resource offset.

The resource offset includes a time-domain offset or a frequency offset or both, and the resource offset is preconfigured or is notified by the base station.

Optionally, when it is mentioned that the first resource and the second resource are at different times, it specifically means the following: the first resource and the second resource belong to different orthogonal frequency division multiplexing OFDM symbols or different timeslots or different subframes or different subframe sets.

Optionally, the third power determining unit 34a is specifically configured to: if a transmit power of the target cell on the second resource is not 0, determine the RSRQ of the target cell according to the RSRP and RSSI; and/or if a transmit power of the target cell on the second resource is 0, determine the SINR of the target cell according to the RSRP and RSSI.

Optionally, the first reference signal includes a discovery reference signal DRS.

The second reference information includes at least one of a channel state information reference signal CSI-RS, a cell-specific reference signal CRS, a reduced cell-specific reference signal RCRS, a primary synchronization signal PSS, a secondary synchronization signal SSS, a positioning reference signal PRS, and a broadcast channel.

Optionally, as shown in FIG. 8, the user equipment 3a further includes: an information reporting unit 36a.

The information reporting unit 36a is configured to report the RSRQ to the base station, so that the base station determines, according to the RSRQ reported by the UE, whether to switch the target cell from the dormant state to the active state, and/or determines, according to the RSRQ reported by the UE, whether to configure the target cell for the UE.

Optionally, the information reporting unit 36a is configured to report the SINR to the base station, so that the base station determines, according to the SINR reported by the UE, whether to switch the target cell from the dormant state to the active state, and/or determines, according to the SINR reported by the UE, whether to configure the target cell for the UE.

Optionally, the information reporting unit 36a is configured to report the RSRQ and SINR to the base station, so that the base station determines, according to the RSRQ and SINR reported by the UE, whether to switch the target cell from the dormant state to the active state, and/or determines, according to the RSRQ and SINR reported by the UE, whether to configure the target cell for the UE.

The user equipment provided by this embodiment of the present invention determines reference signal received quality RSRQ or a signal to interference plus noise ratio SINR of a target cell or both according to a reference signal received power RSRP of the target cell, which is determined by a received power of a first reference signal carried on a first resource, and a received signal strength indicator RSSI of the target cell, which is determined by a total received power on a second resource. In comparison with the prior art in which the RSRQ or SINR of a target cell is measured only according to a CRS or a DRS and an interference environment between neighboring cells in an area is caused to change or vary quickly, the method for radio resource management measurement according to the present invention achieves higher efficiency. In addition, to solve the problem in which the RSRQ or SINR measured by the UE is underestimated in the prior art, a time difference exists between the first resource and the second resource provided by the present invention, so that the RSSI of the target cell does not include the power of a cell in a dormant state (the target cell or a neighboring cell of the target cell or both). Thereby, underestimation of the RSRQ and/or SINR is avoided, and accuracy of radio resource management measurement is further improved.

It should be noted that, for an implementation manner and interaction process of each unit in the user equipment in each of the foregoing embodiments of the present invention, reference may be made to a related description in the corresponding method embodiment.

Figure 9:
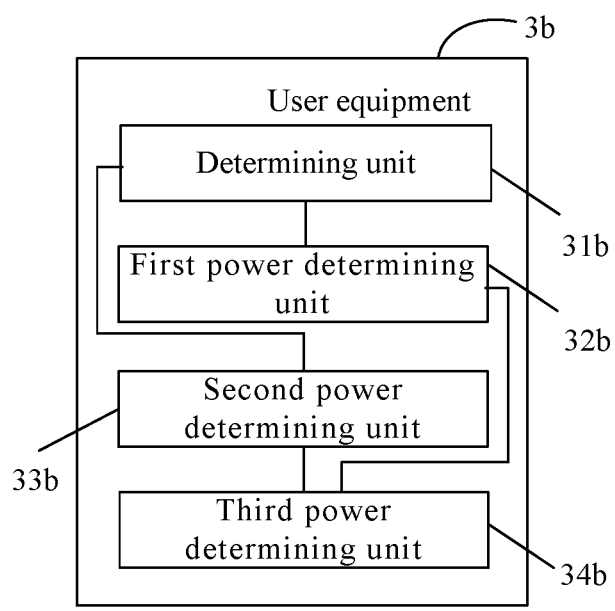
FIG. 9 is a schematic structural diagram of yet another user equipment according to an embodiment of the present disclosure.

An embodiment of the present invention provides a user equipment. The user equipment is used to implement the foregoing method for radio resource management measurement. As shown in FIG. 9, the user equipment 3b includes: a determining unit 31b, a first power determining unit 32b, a second power determining unit 33b, and a third power determining unit 34b.

The determining unit 31b is configured to detect a third reference signal, and determine, according to the detected third reference signal, a target cell corresponding to the detected third reference signal; and configured to detect a first reference signal, and determine, according to the detected first reference signal, a first resource on which the detected first reference signal is located.

The first reference signal includes a discovery reference signal DRS; or optionally, the third reference signal may be a synchronization signal, that is, a PSS or an SSS or a combination thereof. The synchronization signal may also be regarded as a DRS or a part of a DRS. At this time, the UE may determine a cell identifier of the target cell according to the detected PSS or SSS or both. The first reference signal may be at least one of a PRS, a CSI-RS, a CRS, and an RCRS. The first reference signal may be regarded as a DRS or another part of a DRS, and the first reference signal is used for RRM measurement of the target cell.

The first power determining unit 32b is configured to determine a reference signal received power RSRP of the target cell according to a received power of the detected first reference signal carried on the first resource.

The determining unit 31b is further configured to determine a second resource.

The first resource and the second resource are at different times.

Optionally, the number of time units included in the second resource is greater than the number of time units included in the first resource, and the time units included in the second resource are inclusive of the time units included in the first resource, where each of the time units includes any one of an OFDM symbol, a timeslot, a subframe, and a subframe set.

The second resource is used to carry second reference information when the target cell is in an active state, or the second resource is used to not carry second reference information when the target cell is in a dormant state and used to carry the second reference information when the target cell changes from the dormant state to the active state. The foregoing feature of the second resource regarding whether or not to carry the second reference information is also applicable to a neighboring cell of the target cell.

Optionally, the second reference information includes at least one of a channel state information reference signal CSI-RS, a cell-specific reference signal CRS, a reduced cell-specific reference signal RCRS, a primary synchronization signal PSS, a secondary synchronization signal SSS, a positioning reference signal PRS, and a broadcast channel.

The second power determining unit 33b is configured to determine a received signal strength indicator RSSI of the target cell according to a total received power on the second resource.

It should be noted that, specifically two implementation manners are included in a process of acquiring the received signal strength indicator RSSI of the target cell by the second power determining unit 33b. A first implementation manner is: using the total received power on the second resource or the total received power multiplied by a coefficient as the RSSI. A second implementation manner is: adding together the received powers in the time units occupied by the first reference signal and the received powers in the time units occupied by the second reference information, and then dividing the sum by the total number of time units included in the entire second resource to perform averaging, and finally obtaining the RSSI.

The third power determining unit 34b is configured to determine reference signal received quality RSRQ or a signal to interference plus noise ratio SINR of the target cell according to the RSRP and RSSI.

The user equipment provided by this embodiment of the present invention determines reference signal received quality RSRQ or a signal to interference plus noise ratio SINR of a target cell or both according to a reference signal received power RSRP of the target cell, which is determined by a received power of a first reference signal carried on a first resource, and a received signal strength indicator RSSI of the target cell, which is determined by a total received power on a second resource. In comparison with the prior art in which the RSRQ or SINR of a target cell is measured only according to a CRS or a DRS and an interference environment between neighboring cells in an area is caused to change or vary quickly, the method for radio resource management measurement according to the present invention achieves higher efficiency. In addition, to solve the problem in which the RSRQ or SINR measured by the UE is underestimated in the prior art, a time difference exists between the first resource and the second resource provided by the present invention, so that the RSSI of the target cell does not include the power of a cell in a dormant state (the target cell or a neighboring cell of the target cell or both). Thereby, underestimation of the RSRQ and/or SINR is avoided, and accuracy of radio resource management measurement is further improved.

Figure 10:
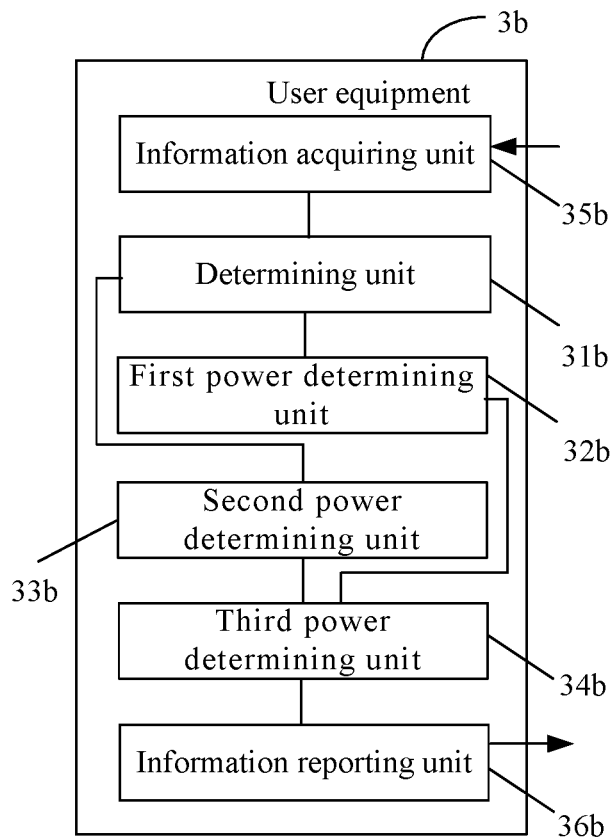
FIG. 10 is a schematic structural diagram of still another user equipment according to an embodiment of the present disclosure.

Optionally, as shown in FIG. 10, the user equipment 3b further includes: an information acquiring unit 35b.

The information acquiring unit 35b is configured to acquire configuration information of the first reference signal.

The configuration information includes a candidate sequence of the first reference signal or a candidate time-frequency resource of the first reference signal or both.

The determining unit 31b is specifically configured to: detect the first reference signal according to the configuration information of the first reference signal; and determine, according to the detected first reference signal, the first resource on which the detected first reference signal is located.

Optionally, the information acquiring unit 35b is configured to acquire configuration information of the third reference signal.

The configuration information includes a candidate sequence of the third reference signal or a candidate time-frequency resource of the third reference signal or both.

The determining unit 31b is specifically configured to: detect the third reference signal according to the configuration information of the third reference signal; and determine, according to the configuration information of the detected third reference signal, the target cell corresponding to the detected third reference signal.

Optionally, the determining unit 31b is specifically configured to determine the second resource according to the first resource and a resource offset.

The resource offset includes a time-domain offset or a frequency offset or both, and the resource offset is preconfigured or is notified by the base station.

Optionally, when it is mentioned that the first resource and the second resource are at different times, it specifically means the following: the first resource and the second resource belong to different orthogonal frequency division multiplexing OFDM symbols or different timeslots or different subframes or different subframe sets.

Optionally, the third power determining unit 34b is specifically configured to: if a transmit power of the target cell on the second resource is not 0, determine the RSRQ of the target cell according to the RSRP and RSSI; and/or if a transmit power of the target cell on the second resource is 0, determine the SINR of the target cell according to the RSRP and RSSI.

Optionally, as shown in FIG. 10, the user equipment 3b further includes: an information reporting unit 36b.

The information reporting unit 36b is configured to report the RSRQ to the base station, so that the base station determines, according to the RSRQ reported by the UE, whether to switch the target cell from the dormant state to the active state, and/or determines, according to the RSRQ reported by the UE, whether to configure the target cell for the UE.

Optionally, the information reporting unit 36b is configured to report the SINR to the base station, so that the base station determines, according to the SINR reported by the UE, whether to switch the target cell from the dormant state to the active state, and/or determines, according to the SINR reported by the UE, whether to configure the target cell for the UE.

Optionally, the information reporting unit 36b is configured to report the RSRQ and SINR to the base station, so that the base station determines, according to the RSRQ and SINR reported by the UE, whether to switch the target cell from the dormant state to the active state, and/or determines, according to the RSRQ and SINR reported by the UE, whether to configure the target cell for the UE.

The user equipment provided by this embodiment of the present invention determines reference signal received quality RSRQ or a signal to interference plus noise ratio SINR of a target cell or both according to a reference signal received power RSRP of the target cell, which is determined by a received power of a first reference signal carried on a first resource, and a received signal strength indicator RSSI of the target cell, which is determined by a total received power on a second resource. In comparison with the prior art in which the RSRQ or SINR of a target cell is measured only according to a CRS or a DRS and an interference environment between neighboring cells in an area is caused to change or vary quickly, the method for radio resource management measurement according to the present invention achieves higher efficiency. In addition, to solve the problem in which the RSRQ or SINR measured by the UE is underestimated in the prior art, a time difference exists between the first resource and the second resource provided by the present invention, so that the RSSI of the target cell does not include the power of a cell in a dormant state (the target cell or a neighboring cell of the target cell or both). Thereby, underestimation of the RSRQ and/or SINR is avoided, and accuracy of radio resource management measurement is further improved.

It should be noted that, for an implementation manner and interaction process of each unit in the user equipment in each of the foregoing embodiments of the present invention, reference may be made to a related description in the corresponding method embodiment.

Figure 11:
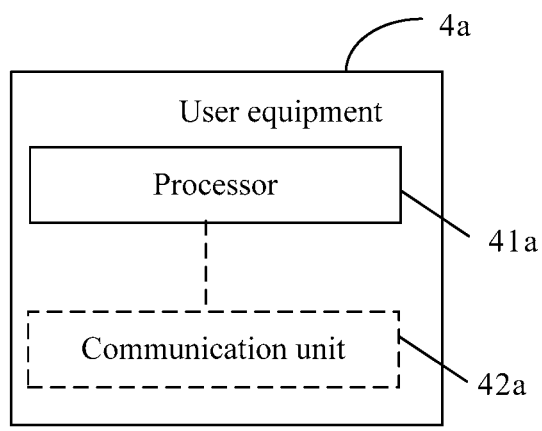
FIG. 11 is a schematic structural diagram of a user equipment according to another embodiment of the present disclosure.

An embodiment of the present invention provides a user equipment. The user equipment is used to implement the foregoing method for radio resource management measurement. As shown in FIG. 11, the user equipment 4a includes: a processor 41a.

The processor 41a is configured to detect a first reference signal, and determine, according to the detected first reference signal, a target cell corresponding to the detected first reference signal and a first resource on which the detected first reference signal is located.

The processor 41a is further configured for the UE to determine a reference signal received power RSRP of the target cell according to a received power of the detected first reference signal carried on the first resource.

The processor 41a is further configured to determine a second resource.

The first resource and the second resource are at different times.

The second resource is used to carry second reference information when the target cell is in an active state, or the second resource is used to not carry second reference information when the target cell is in a dormant state and used to carry the second reference information when the target cell changes from the dormant state to the active state. The foregoing feature of the second resource regarding whether or not to carry the second reference information is also applicable to a neighboring cell of the target cell.

The processor 41a is further configured to determine a received signal strength indicator RSSI of the target cell according to a total received power on the second resource.

The processor 41a is further configured to determine reference signal received quality RSRQ or a signal to interference plus noise ratio SINR of the target cell according to the RSRP and RSSI.

The user equipment provided by this embodiment of the present invention determines reference signal received quality RSRQ or a signal to interference plus noise ratio SINR of a target cell or both according to a reference signal received power RSRP of the target cell, which is determined by a received power of a first reference signal carried on a first resource, and a received signal strength indicator RSSI of the target cell, which is determined by a total received power on a second resource. In comparison with the prior art in which the RSRQ or SINR of a target cell is measured only according to a CRS or a DRS and an interference environment between neighboring cells in an area is caused to change or vary quickly, the method for radio resource management measurement according to the present invention achieves higher efficiency. In addition, to solve the problem in which the RSRQ or SINR measured by the UE is underestimated in the prior art, a time difference exists between the first resource and the second resource provided by the present invention, so that the RSSI of the target cell does not include the power of a cell in a dormant state (the target cell or a neighboring cell of the target cell or both). Thereby, underestimation of the RSRQ and/or SINR is avoided, and accuracy of radio resource management measurement is further improved.

Optionally, the processor 41*a* is further configured to: acquire configuration information of the first reference signal, where the configuration information includes a candidate sequence of the first reference signal or a candidate time-frequency resource of the first reference signal or both; detect the first reference signal according to the configuration information of the first reference signal; and determine, according to the configuration information of the detected first reference signal, the target cell corresponding to the detected first reference signal and the first resource on which the detected first reference signal is located.

Optionally, the processor 41*a* is further configured to determine the second resource according to the first resource and a resource offset.

The resource offset includes a time-domain offset or a frequency offset or both, and the resource offset is pre-configured or is notified by a base station.

Optionally, when it is mentioned that the first resource and the second resource are at different times, it specifically means the following: the first resource and the second resource belong to different orthogonal frequency division multiplexing OFDM symbols or different timeslots or different subframes or different subframe sets.

Optionally, the processor 41*a* is further configured to: if a transmit power of the target cell on the second resource is not 0, determine the RSRQ of the target cell according to the RSRP and RSSI; and/or if a transmit power of the target cell on the second resource is 0, determine the SINR of the target cell according to the RSRP and RSSI.

Optionally, the first reference signal includes a discovery reference signal DRS.

The second reference information includes at least one of a channel state information reference signal CSI-RS, a cell-specific reference signal CRS, a reduced cell-specific reference signal RCRS, a primary synchronization signal PSS, a secondary synchronization signal SSS, a positioning reference signal PRS, and a broadcast channel.

Optionally, the user equipment 4*a* further includes: a communication unit 42*a*.

The communication unit 42*a* is configured to report the RSRQ to the base station, so that the base station determines, according to the RSRQ reported by the UE, whether to switch the target cell from the dormant state to the active state, and/or determines, according to the RSRQ reported by the UE, whether to configure the target cell for the UE.

Optionally, the communication unit 42*a* is configured to report the SINR to the base station, so that the base station determines, according to the SINR reported by the UE, whether to switch the target cell from the dormant state to the active state, and/or determines, according to the SINR reported by the UE, whether to configure the target cell for the UE.

Optionally, the communication unit 42*a* is configured to report the RSRQ and SINR to the base station, so that the base station determines, according to the RSRQ and SINR reported by the UE, whether to switch the target cell from the dormant state to the active state, and/or determines, according to the RSRQ and SINR reported by the UE, whether to configure the target cell for the UE.

The user equipment provided by this embodiment of the present invention determines reference signal received quality RSRQ or a signal to interference plus noise ratio SINR of a target cell or both according to a reference signal received power RSRP of the target cell, which is determined by a received power of a first reference signal carried on a first resource, and a received signal strength indicator RSSI of the target cell, which is determined by a total received power on a second resource. In comparison with the prior art in which the RSRQ or SINR of a target cell is measured only according to a CRS or a DRS and an interference environment between neighboring cells in an area is caused to change or vary quickly, the method for radio resource management measurement according to the present invention achieves higher efficiency. In addition, to solve the problem in which the RSRQ or SINR measured by the UE is underestimated in the prior art, a time difference exists between the first resource and the second resource provided by the present invention, so that the RSSI of the target cell does not include the power of a cell in a dormant state (the target cell or a neighboring cell of the target cell or both). Thereby, underestimation of the RSRQ and/or SINR is avoided, and accuracy of radio resource management measurement is further improved.

It should be noted that, for an implementation manner and interaction process of each unit in the user equipment in each of the foregoing embodiments of the present invention, reference may be made to a related description in the corresponding method embodiment.

Figure 12:
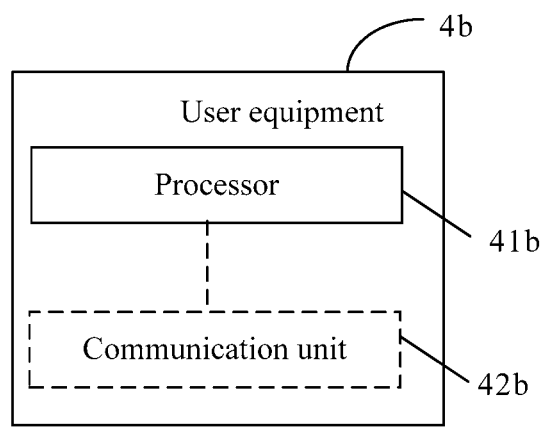
FIG. 12 is a schematic structural diagram of another user equipment according to another embodiment of the present disclosure.

An embodiment of the present invention provides a user equipment. The user equipment is used to implement the foregoing method for radio resource management measurement. As shown in FIG. 12, the user equipment 4*b* includes: a processor 41*b*.

The processor 41*b* is configured to detect a third reference signal, and determine, according to the detected third reference signal, a target cell corresponding to the detected third reference signal; and configured to detect a first reference signal, and determine, according to the detected first reference signal, a first resource on which the detected first reference signal is located.

The first reference signal includes a discovery reference signal DRS. Alternatively, optionally, the third reference signal may be a synchronization signal, that is, a PSS or an SSS or a combination thereof. The synchronization signal may also be regarded as a DRS or a part of a DRS. At this time, the UE may determine a cell identifier of the target cell according to the detected PSS or SSS or both. The first reference signal may be at least one of a PRS, a CSI-RS, a CRS, and an RCRS. The first reference signal may be regarded as a DRS or another part of a DRS, and the first reference signal is used for RRM measurement of the target cell.

The processor 41*b* is further configured for the UE to determine a reference signal received power RSRP of the target cell according to a received power of the detected first reference signal carried on the first resource.

The processor 41*b* is further configured to determine a second resource.

The first resource and the second resource are at different times.

Optionally, the number of time units included in the second resource is greater than the number of time units included in the first resource, and the time units included in the second resource are inclusive of the time units included in the first resource, where each of the time units includes any one of an OFDM symbol, a timeslot, a subframe, and a subframe set.

The second resource is used to carry second reference information when the target cell is in an active state, or the second resource is used to not carry second reference information when the target cell is in a dormant state and used to carry the second reference information when the target cell changes from the dormant state to the active state. The foregoing feature of the second resource regarding whether or not to carry the second reference information is also applicable to a neighboring cell of the target cell.

Optionally, the second reference information includes at least one of a channel state information reference signal CSI-RS, a cell-specific reference signal CRS, a reduced cell-specific reference signal RCRS, a primary synchronization signal PSS, a secondary synchronization signal SSS, a positioning reference signal PRS, and a broadcast channel.

The processor 41b is further configured to determine a received signal strength indicator RSSI of the target cell according to a total received power on the second resource.

It should be noted that, specifically two implementation manners are included in a process of acquiring the received signal strength indicator RSSI of the target cell by the processor 41b. A first implementation manner is: using the total received power on the second resource or the total received power multiplied by a coefficient as the RSSI. A second implementation manner is: adding together the received powers in the time units occupied by the first reference signal and the received powers in the time units occupied by the second reference information, and then dividing the sum by the total number of time units included in the entire second resource to perform averaging, and finally obtaining the RSSI.

The processor 41b is further configured to determine reference signal received quality RSRQ or a signal to interference plus noise ratio SINR of the target cell according to the RSRP and RSSI.

The user equipment provided by this embodiment of the present invention determines reference signal received quality RSRQ or a signal to interference plus noise ratio SINR of a target cell or both according to a reference signal received power RSRP of the target cell, which is determined by a received power of a first reference signal carried on a first resource, and a received signal strength indicator RSSI of the target cell, which is determined by a total received power on a second resource. In comparison with the prior art in which the RSRQ or SINR of a target cell is measured only according to a CRS or a DRS and an interference environment between neighboring cells in an area is caused to change or vary quickly, the method for radio resource management measurement according to the present invention achieves higher efficiency. In addition, to solve the problem in which the RSRQ or SINR measured by the UE is underestimated in the prior art, a time difference exists between the first resource and the second resource provided by the present invention, so that the RSSI of the target cell does not include the power of a cell in a dormant state (the target cell or a neighboring cell of the target cell or both). Thereby, underestimation of the RSRQ and/or SINR is avoided, and accuracy of radio resource management measurement is further improved.

Optionally, the processor 41b is further configured to: acquire configuration information of the first reference signal, where the configuration information includes a candidate sequence of the first reference signal or a candidate time-frequency resource of the first reference signal or both; detect the first reference signal according to the configuration information of the first reference signal; and determine, according to the detected first reference signal, the first resource on which the detected first reference signal is located.

The processor 41b is further configured to: acquire configuration information of the third reference signal, where the configuration information includes a candidate sequence of the third reference signal or a candidate time-frequency resource of the third reference signal or both; detect the third reference signal according to the configuration information of the third reference signal; and determine, according to the configuration information of the detected third reference signal, the target cell corresponding to the detected third reference signal.

Optionally, the processor 41b is further configured to determine the second resource according to the first resource and a resource offset.

The resource offset includes a time-domain offset or a frequency offset or both, and the resource offset is pre-configured or is notified by a base station.

Optionally, when it is mentioned that the first resource and the second resource are at different times, it specifically means the following: the first resource and the second resource belong to different orthogonal frequency division multiplexing OFDM symbols or different timeslots or different subframes or different subframe sets.

Optionally, the processor 41a is further configured to: if a transmit power of the target cell on the second resource is not 0, determine the RSRQ of the target cell according to the RSRP and RSSI; and/or if a transmit power of the target cell on the second resource is 0, determine the SINR of the target cell according to the RSRP and RSSI.

Optionally, the user equipment 4b further includes: a communication unit 42b.

The communication unit 42b is configured to report the RSRQ to the base station, so that the base station determines, according to the RSRQ reported by the UE, whether to switch the target cell from the dormant state to the active state, and/or determines, according to the RSRQ reported by the UE, whether to configure the target cell for the UE.

Optionally, the communication unit 42b is configured to report the SINR to the base station, so that the base station determines, according to the SINR reported by the UE, whether to switch the target cell from the dormant state to the active state, and/or determines, according to the SINR reported by the UE, whether to configure the target cell for the UE.

Optionally, the communication unit 42b is configured to report the RSRQ and SINR to the base station, so that the base station determines, according to the RSRQ and SINR reported by the UE, whether to switch the target cell from the dormant state to the active state, and/or determines, according to the RSRQ and SINR reported by the UE, whether to configure the target cell for the UE.

The user equipment provided by this embodiment of the present invention determines reference signal received quality RSRQ or a signal to interference plus noise ratio SINR of a target cell or both according to a reference signal received power RSRP of the target cell, which is determined by a received power of a first reference signal carried on a first resource, and a received signal strength indicator RSSI of the target cell, which is determined by a total received power on a second resource. In comparison with the prior art in which the RSRQ or SINR of a target cell is measured only according to a CRS or a DRS and an interference environment between neighboring cells in an area is caused to change or vary quickly, the method for radio resource management measurement according to the present invention achieves higher efficiency. In addition, to solve the problem in which the RSRQ or SINR measured by the UE is underestimated in the prior art, a time difference exists between the first resource and the second resource provided by the present invention, so that the RSSI of the target cell does not include the power of a cell in a dormant state (the target cell or a neighboring cell of the target cell or both). Thereby, underestimation of the RSRQ and/or SINR is avoided, and accuracy of radio resource management measurement is further improved.

It should be noted that, for an implementation manner and interaction process of each unit in the user equipment in each of the foregoing embodiments of the present invention, reference may be made to a related description in the corresponding method embodiment.

Figure 13:
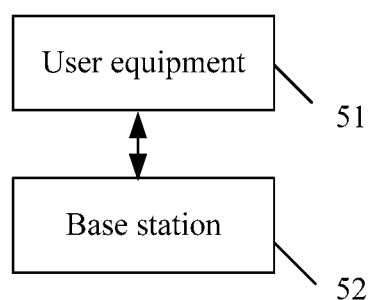
FIG. 13 is a schematic structural diagram of a system for radio resource management measurement according to an embodiment of the present disclosure.

An embodiment of the present invention provides a system for radio resource management measurement. As shown in FIG. 13, the system 5 for radio resource management side measurement includes: a user equipment UE 51 and a base station 52.

The UE 51 is configured to: detect a first reference signal, and determine, according to the detected first reference signal, a target cell corresponding to the detected first reference signal and a first resource on which the detected first reference signal is located; further configured to determine a reference signal received power RSRP of the target cell according to a received power of the detected first reference signal carried on the first resource; further configured to determine a second resource; further configured to determine a received signal strength indicator RSSI of the target cell according to a total received power on the second resource, where the first resource and the second resource are at different times, where the second resource is used to carry second reference information when the target cell is in an active state, or the second resource is used to not carry second reference information when the target cell is in a dormant state and used to carry the second reference information when the target cell changes from the dormant state to the active state; further configured to determine reference signal received quality RSRQ or a signal to interference plus noise ratio SINR of the target cell according to the RSRP and RSSI; and further configured to report the RSRQ or SINR or both to the base station 52; or the UE 51 is configured to: detect a first reference signal, and determine, according to the detected first reference signal, a first resource on which the detected first reference signal is located; and configured to detect a third reference signal, and determine, according to the detected third reference signal, a target cell corresponding to the detected third reference signal; further configured to determine a reference signal received power RSRP of the target cell according to a received power of the detected first reference signal carried on the first resource; further configured to determine a second resource; further configured to determine a received signal strength indicator RSSI of the target cell according to a total received power on the second resource, where the first resource and the second resource are at different times, where the second resource is used to carry second reference information when the target cell is in an active state, or the second resource is used to not carry second reference information when the target cell is in a dormant state and used to carry the second reference information when the target cell changes from the dormant state to the active state; further configured to determine reference signal received quality RSRQ or a signal to interference plus noise ratio SINR of the target cell according to the RSRP and RSSI; and further configured to report the RSRQ or SINR or both to the base station 52. The foregoing feature of the second resource regarding whether or not to carry the second reference information is also applicable to a neighboring cell of the target cell.

The base station 52 is configured to determine, according to the RSRQ reported by the UE, whether to switch the target cell from the dormant state to the active state, and/or determine, according to the RSRQ reported by the UE, whether to configure the target cell for the UE;

or configured to determine, according to the SINR reported by the UE, whether to switch the target cell from the dormant state to the active state, and/or determine, according to the SINR reported by the UE, whether to configure the target cell for the UE;

or configured to determine, according to the RSRQ and SINR that are reported by the UE, whether to switch the target cell from the dormant state to the active state, and/or determine, according to the RSRQ and SINR reported by the UE, whether to configure the target cell for the UE.

In the system for radio resource management side measurement according to this embodiment of the present invention, reference signal received quality RSRQ or a signal to interference plus noise ratio SINR of a target cell or both are determined according to a reference signal received power RSRP of the target cell, which is determined by a received power of a first reference signal carried on a first resource, and a received signal strength indicator RSSI of the target cell, which is determined by a total received power on a second resource. In comparison with the prior art in which the RSRQ or SINR of a target cell is measured only according to a CRS or a DRS and an interference environment between neighboring cells in an area is caused to change or vary quickly, the method for radio resource management measurement according to the present invention achieves higher efficiency. In addition, to solve the problem in which the RSRQ or SINR measured by the UE is underestimated in the prior art, a time difference exists between the first resource and the second resource provided by the present invention, so that the RSSI of the target cell does not include the power of a cell in a dormant state (the target cell or a neighboring cell of the target cell or both). Thereby, underestimation of the RSRQ and/or SINR is avoided, and accuracy of radio resource management measurement is further improved.

It may be clearly understood by a person skilled in the art that, for the purpose of convenient and brief description, division of the foregoing functional modules is merely used as an example, and in an actual implementation, the foregoing functions may be assigned to different functional modules according to an actual need, that is, an internal structure of the apparatus is divided into different functional modules, to complete all or a part of the functions described above. For a detailed working process of the foregoing system, apparatus, and unit, reference may be made to a corresponding process in the foregoing method embodiments, and details are not described herein again.

In the several embodiments provided in the present application, it should be understood that the disclosed system, apparatus, and method may be implemented in other manners. For example, the described apparatus embodiment is merely exemplary. For example, the module or unit division is merely logical function division and may be other division in actual implementation. For example, a plurality of units or components may be combined or integrated into another system, or some features may be ignored or not performed. Furthermore, the displayed or discussed mutual couplings or direct couplings or communication connections may be implemented through some interfaces. The indirect couplings or communication connections between the apparatuses or units may be implemented in electronic, mechanical, or other forms.

The units described as separate parts may or may not be physically separate, and parts displayed as units may or may not be physical units, may be located in one position, or may be distributed on a plurality of network units. A part or all of the units may be selected according to an actual need to achieve the objectives of the solutions of the embodiments.

In addition, functional units in the embodiments of the present application may be integrated into one processing unit, or each of the units may exist alone physically, or two or more units are integrated into one unit. The integrated unit may be implemented in a form of hardware, or may be implemented in a form of a software functional unit.

When the integrated unit is implemented in a form of a software functional unit and sold or used as an independent product, the integrated unit may be stored in a computer-readable storage medium. Based on such an understanding, the technical solutions of the present application essentially, or the part contributing to the prior art, or all or a part of the technical solutions may be implemented in the form of a software product. The software product is stored in a storage medium and includes several instructions for instructing a computer device (which may be a personal computer, a server, or a network device) or a processor to perform all or a part of the steps of the methods described in the embodiments of the present application. The foregoing storage medium includes any medium that can store program code, such as a USB flash drive, a removable hard disk, a read-only memory (ROM), a random access memory (RAM), a magnetic disk, or an optical disc.

The foregoing embodiments are merely intended for describing the technical solutions of the present application other than limiting the present application. Although the present application is described in detail with reference to the foregoing embodiments, persons of ordinary skill in the art should understand that they may still make modifications to the technical solutions described in the foregoing embodiments or make equivalent replacements to some technical features thereof, without departing from the scope of the technical solutions of the embodiments of the present application.

What is claimed is:

1. A user equipment (UE) comprising:
a processor; and
a memory coupled to the processor, wherein the memory stores instructions that, when executed by the processor, cause the processor to be configured to:
detect a first reference signal comprising a discovery reference signal (DRS), and determine, according to the detected first reference signal, a first resource on which the detected first reference signal is located;
determine a reference signal received power (RSRP) of a target cell according to a received power of the detected first reference signal carried on the first resource;
determine a second resource, wherein the second resource carries second reference information when (a) the target cell or a neighboring cell of the target cell, or both, are in an active state, or (b) the target cell changes from the dormant state to the active state, wherein the second reference information comprises:
a) a channel state information reference signal (CSI-RS), and
b) a secondary synchronization signal (SSS),
determine a received signal strength indicator (RSSI) of the target cell according to a total received power on the second resource, wherein the first resource and the second resource are at different times; and
determine reference signal received quality (RSRQ) or a signal to interference plus noise ratio (SINR) of the target cell according to the RSRP and RSSI.

2. The user equipment according to claim 1, wherein the processor is further configured to detect a third reference signal, and determine, according to the detected third reference signal, the target cell corresponding to the detected third reference signal.

3. The user equipment according to claim 1, wherein a number of time units comprised in the second resource is greater than a number of time units comprised in the first resource, and the time units comprised in the second resource are inclusive of the time units comprised in the first resource, wherein the time units comprise any one of an orthogonal frequency division multiplexing (OFDM) symbol, a timeslot, a subframe, and a subframe set.

4. The user equipment according to claim 1, wherein:
the processor is further configured to determine the second resource according to the first resource and a resource offset, wherein the resource offset comprises a time-domain offset or a frequency offset or both, and the resource offset is pre-configured or is notified by a base station.

5. The user equipment according to claim 1, wherein the processor is further configured to:
if a transmit power of the target cell on the second resource is not 0, determine the RSRQ of the target cell according to the RSRP and RSSI; and
if a transmit power of the target cell on the second resource is 0, determine the SINR of the target cell according to the RSRP and RSSI.

6. The user equipment according to claim 1, further comprising:
a transmitter coupled to the processor and configured to transmit the RSRQ to a base station, wherein the RSRQ is used by the base station to determine whether to switch the target cell from the dormant state to the active state, and/or to determine whether to configure the target cell for the UE.

7. A method for radio resource management measurement, comprising:
detecting, by a user equipment (UE), a first reference signal comprising a discovery reference signal (DRS), and determining, according to the detected first reference signal, a first resource on which the detected first reference signal is located;
determining, by the UE, a reference signal received power (RSRP) of a target cell according to a received power of the detected first reference signal carried on the first resource;
determining, by the UE, a second resource, wherein the second resource carries second reference information when (a) the target cell or a neighboring cell of the target cell, or both, are in an active state, or (b) the target cell changes from the dormant state to the active state, wherein the second reference information comprises:
a) channel state information reference signal (CSI-RS), and
b) a secondary synchronization signal (SSS),
determining, by the UE, a received signal strength indicator (RSSI) of the target cell according to a total received power on the second resource; and
determining, by the UE, reference signal received quality (RSRQ) or a signal to interference plus noise ratio (SINR) of the target cell or both according to the RSRP and RSSI.

8. The method according to claim 7, further comprising:
detecting, by the UE, a third reference signal, and determining, according to the detected third reference signal, a target cell corresponding to the detected third reference signal.

9. The method according to claim 7, wherein a number of time units comprised in the second resource is greater than a number of time units comprised in the first resource, and the time units comprised in the second resource are inclusive of the time units comprised in the first resource, wherein the time units are any one of an orthogonal frequency division multiplexing (OFDM) symbol, a timeslot, a subframe, and a subframe set.

10. The method according to claim 7, wherein determining the RSRQ or the SINR of the target cell or both according to the RSRP and RSSI, further comprises:
if a transmit power of the target cell on the second resource is not 0, determining, by the UE, the RSRQ of the target cell according to the RSRP and RSSI; and
if a transmit power of the target cell on the second resource is 0, determining, by the UE, the SINR of the target cell according to the RSRP and RSSI.

11. The method according to claim 7, further comprising:
reporting, by the UE, the RSRQ to a base station, wherein the RSRQ is used by the base station to determine whether to switch the target cell from the dormant state to the active state, and/or to determine whether to configure the target cell for the UE.

12. The method according to claim 7, further comprising:
reporting, by the UE, the SINR to a base station, wherein the SINR is used by the base station to determine whether to switch the target cell from the dormant state to the active state, and/or to determine whether to configure the target cell for the UE.

13. A non-transitory, computer readable medium at user equipment that stores executable instructions that, when executed by a processor, cause the user equipment (UE) to perform the following method for radio resource management measurement:
detecting a first reference signal;
determining, according to the detection of the first reference signal, a first resource on which the first reference signal is located, wherein the first reference signal comprises at least one of a cell-specific reference signal (CRS), and a channel state information reference signal (CSI-RS);
determining a reference signal received power (RSRP) of a target cell according to a received power of the first reference signal carried on the first resource;
determining a second resource, wherein the second resource (a) carries a second reference information when the neighboring cell of the target cell changes from the dormant state to the active state and (b) does not carry the second reference information when a neighboring cell of the target cell is in a dormant state, wherein the second reference information includes at least one of a primary synchronization signal (PSS), and a secondary synchronization signal (SSS), wherein the second reference information comprises a channel state information reference signal (CSI-RS) and a secondary synchronization signal (SSS);
determining a received signal strength indicator (RSSI) of the target cell according to a total received power on the second resource; and
determining reference signal received quality (RSRQ) or a signal to interference plus noise ratio (SINR) of the target cell, or both, according to the RSRP and RSSI.

14. The non-transitory, computer readable medium according to claim 13, further including instructions for:
Detecting a third reference signal, and determining, according to the detected third reference signal, a target cell corresponding to the detected third reference signal.

15. The non-transitory, computer readable medium according to claim 13, wherein the instructions for determining the RSRQ or SINR of the target cell, or both, according to the RSRP and RSSI, further provide for:
if a transmit power of the target cell on the second resource is not 0, determining the RSRQ of the target cell according to the RSRP and RSSI; and/or
if a transmit power of the target cell on the second resource is 0, determining the SINR of the target cell according to the RSRP and RSSI.

16. The non-transitory, computer readable medium according to claim 13, wherein the first reference signal comprises a discovery reference signal (DRS).

17. The non-transitory, computer readable medium according to claim 13, wherein after determining the RSRQ or the SINR of the target cell, or both, according to the RSRP and RSSI, the instructions further provide for:
reporting, by the UE, the RSRQ to the base station, where the base station determines according to the RSRQ reported by the UE whether to switch the target cell from the dormant state to the active state, and/or to configure the target cell for the UE.

18. The non-transitory, computer readable medium according to claim 13, wherein after determining the RSRQ or the SINR of the target cell, or both, according to the RSRP and RSSI, the instructions further provide for:
reporting, by the UE, the SINR to the base station, where the base station determines according to the SINR reported by the UE whether to switch the target cell from the dormant state to the active state, and/or to configure the target cell for the UE.

* * * * *

UNITED STATES PATENT AND TRADEMARK OFFICE
CERTIFICATE OF CORRECTION

PATENT NO. : 10,045,986 B2
APPLICATION NO. : 15/140299
DATED : August 14, 2018
INVENTOR(S) : Lei Guan et al.

Page 1 of 1

It is certified that error appears in the above-identified patent and that said Letters Patent is hereby corrected as shown below:

In the Claims

Column 40, Claim 7, Line 58, "a) channel state" should read --a) a channel state--

Signed and Sealed this
Sixth Day of August, 2019

Andrei Iancu
*Director of the United States Patent and Trademark Office*